(12) United States Patent
Adams et al.

(10) Patent No.: US 11,497,399 B2
(45) Date of Patent: Nov. 15, 2022

(54) IMPLANTABLE INTRAOCULAR PRESSURE SENSORS AND METHODS OF USE

(71) Applicant: QURA, INC., Sudbury, MA (US)

(72) Inventors: Douglas P. Adams, Sudbury, MA (US); Celso Tello, New York, NY (US); Marcel David Ackermann, Neuchâtel (CH); Jean-Noël Fehr, Neuchâtel (CH)

(73) Assignee: Qura, Inc., Framingham, MA (US)

( * ) Notice: Subject to any disclaimer, the term of this patent is extended or adjusted under 35 U.S.C. 154(b) by 1009 days.

(21) Appl. No.: 16/302,750

(22) PCT Filed: May 31, 2017

(86) PCT No.: PCT/US2017/035247
§ 371 (c)(1),
(2) Date: Nov. 19, 2018

(87) PCT Pub. No.: WO2017/210316
PCT Pub. Date: Dec. 7, 2017

(65) Prior Publication Data
US 2019/0175015 A1 Jun. 13, 2019

Related U.S. Application Data

(60) Provisional application No. 62/343,593, filed on May 31, 2016.

(51) Int. Cl.
*A61B 3/16* (2006.01)
*A61B 5/00* (2006.01)
(Continued)

(52) U.S. Cl.
CPC ............ *A61B 3/16* (2013.01); *A61B 3/00* (2013.01); *A61B 5/00* (2013.01); *A61B 5/0004* (2013.01);
(Continued)

(58) Field of Classification Search
CPC ........ A61B 3/16; A61B 5/0031; A61B 5/6861
See application file for complete search history.

(56) References Cited

U.S. PATENT DOCUMENTS

| 4,206,762 A | 6/1980 | Cosman |
| 4,834,750 A | 5/1989 | Gupta |

(Continued)

FOREIGN PATENT DOCUMENTS

| AU | 2018200978 B2 | 3/2018 |
| AU | 2016311449 A1 | 4/2018 |

(Continued)

OTHER PUBLICATIONS

Araci et al., "An implantable microfluidic device for self-monitoring of intraocular pressure." Nature medicine 20.9 (2014): 1074-1078.

(Continued)

*Primary Examiner* — Daniel L Cerioni
*Assistant Examiner* — Raymond P Dulman
(74) *Attorney, Agent, or Firm* — Smith Baluch LLP

(57) ABSTRACT

Intraocular pressure sensors, systems, and methods of use. Implantable intraocular pressure sensing devices that are hermetically sealed and adapted to wirelessly communicate with an external device. The implantable devices can include a hermetically sealed housing, the hermetically sealed housing including therein: an antenna in electrical communication with a rechargeable power source, the rechargeable power source in electrical communication with an ASIC, and the ASIC in electrical communication with a pressure sensor.

36 Claims, 19 Drawing Sheets

(51) Int. Cl.
  *A61B 3/00* (2006.01)
  *A61B 5/24* (2021.01)
  *A61L 31/08* (2006.01)
  *A61L 31/14* (2006.01)
  *A61L 33/00* (2006.01)
  *A61L 33/18* (2006.01)

(52) U.S. Cl.
  CPC .............. *A61B 5/0031* (2013.01); *A61B 5/24* (2021.01); *A61B 5/6861* (2013.01); *A61L 31/088* (2013.01); *A61L 31/145* (2013.01); *A61L 33/0064* (2013.01); *A61L 33/18* (2013.01)

(56) References Cited

U.S. PATENT DOCUMENTS

| | | | |
|---|---|---|---|
| 4,922,913 A | 5/1990 | Waters et al. | |
| 5,005,577 A | 4/1991 | Frenkel | |
| 5,179,953 A | 1/1993 | Kursar | |
| 5,607,433 A | 3/1997 | Polla et al. | |
| 6,083,174 A | 7/2000 | Brehmeier Flick et al. | |
| 6,152,885 A | 11/2000 | Taepke | |
| 6,168,575 B1 | 1/2001 | Soltanpour | |
| 6,193,656 B1 | 2/2001 | Jeffries et al. | |
| 6,443,893 B1 | 9/2002 | Schnakenberg et al. | |
| 6,447,449 B1 | 9/2002 | Fleischman et al. | |
| 6,544,193 B2 | 4/2003 | Abreu | |
| 6,579,235 B1 | 6/2003 | Abita et al. | |
| 6,613,088 B1 | 9/2003 | Bablzhayev | |
| 6,710,355 B2 | 3/2004 | Youngner | |
| 6,712,764 B2 | 3/2004 | Jeffries et al. | |
| 6,712,772 B2 | 3/2004 | Cohen et al. | |
| 6,749,568 B2 | 6/2004 | Fleischman et al. | |
| 6,796,942 B1 | 9/2004 | Kreiner et al. | |
| 6,802,811 B1 | 10/2004 | Slepian | |
| 6,890,300 B2 | 5/2005 | Lloyd et al. | |
| 6,939,299 B1 | 9/2005 | Petersen et al. | |
| 6,976,959 B2 | 12/2005 | Fresco | |
| 6,981,958 B1 | 1/2006 | Gharib et al. | |
| 7,026,997 B2 | 4/2006 | Rahola | |
| 7,037,335 B2 | 5/2006 | Freeman et al. | |
| 7,131,945 B2 | 11/2006 | Fink et al. | |
| 7,137,952 B2 | 11/2006 | Leonardi et al. | |
| 7,148,850 B2 | 12/2006 | Puente Baliarda et al. | |
| 7,161,484 B2 | 1/2007 | Tsoukalis | |
| 7,252,006 B2 | 8/2007 | Tai et al. | |
| 7,256,695 B2 | 8/2007 | Hamel et al. | |
| 7,273,457 B2 | 9/2007 | Penner | |
| 7,364,564 B2 | 4/2008 | Sniegowski et al. | |
| 7,574,792 B2 * | 8/2009 | O'Brien | A61B 5/076 29/605 |
| 7,595,723 B2 | 9/2009 | Heitzmann et al. | |
| 7,686,762 B1 | 3/2010 | Najafi et al. | |
| 7,724,148 B2 | 5/2010 | Samuelsson et al. | |
| RE42,378 E | 5/2011 | Wolinsky et al. | |
| 7,959,570 B2 | 6/2011 | Enikov et al. | |
| 8,123,687 B2 | 2/2012 | Dacquay et al. | |
| 8,182,435 B2 | 5/2012 | Dacquay et al. | |
| 8,206,440 B2 | 6/2012 | Guarnieri | |
| 8,313,811 B2 | 11/2012 | Hogg et al. | |
| 8,313,819 B2 | 11/2012 | Hogg et al. | |
| 8,361,591 B2 | 1/2013 | Hogg et al. | |
| 8,382,677 B2 | 2/2013 | Bodecker et al. | |
| 8,424,388 B2 | 4/2013 | Mattes et al. | |
| 8,442,641 B2 | 5/2013 | Gross et al. | |
| 8,475,374 B2 | 7/2013 | Irazoqui et al. | |
| 8,549,925 B2 | 10/2013 | Tai et al. | |
| 8,551,163 B2 | 10/2013 | Aber et al. | |
| 8,578,795 B2 | 11/2013 | Crivelli | |
| 8,593,107 B2 | 11/2013 | Penner et al. | |
| 8,795,712 B2 | 8/2014 | de Juan et al. | |
| 8,894,578 B2 | 11/2014 | Wong et al. | |
| 8,901,775 B2 | 12/2014 | Armstrong et al. | |
| 8,926,510 B2 | 1/2015 | Marshall et al. | |
| 8,926,524 B2 | 1/2015 | Chen et al. | |
| 8,938,293 B2 | 1/2015 | Root et al. | |
| 9,022,968 B2 | 5/2015 | Passaglia | |
| 9,041,416 B2 | 5/2015 | Park et al. | |
| 9,078,613 B2 | 7/2015 | Irazoqui et al. | |
| 9,107,592 B2 | 8/2015 | Litt et al. | |
| 9,161,929 B2 | 10/2015 | Ghebremeskel et al. | |
| 9,173,564 B2 | 11/2015 | Choo et al. | |
| 9,220,461 B2 | 12/2015 | Samuelsson et al. | |
| 9,247,577 B2 | 1/2016 | Lee et al. | |
| 9,259,309 B2 | 2/2016 | Fehr et al. | |
| 9,271,677 B2 | 3/2016 | Leonardi | |
| 9,295,389 B2 | 3/2016 | Sanchez et al. | |
| 9,301,082 B2 | 3/2016 | Meyers et al. | |
| 9,307,905 B2 | 4/2016 | Varel et al. | |
| 9,339,187 B2 | 5/2016 | Rickard | |
| 9,341,530 B2 | 5/2016 | Lee et al. | |
| 9,468,522 B2 | 10/2016 | Scholten | |
| 9,596,988 B2 | 3/2017 | Irazoqui et al. | |
| 9,662,021 B2 | 5/2017 | Chow et al. | |
| 9,730,638 B2 | 8/2017 | Haffner et al. | |
| 9,907,694 B2 | 3/2018 | Clarke et al. | |
| 10,044,227 B2 | 8/2018 | Chappell et al. | |
| 10,206,569 B1 | 2/2019 | Peyman | |
| 10,251,779 B2 | 4/2019 | Lerner | |
| 10,271,945 B2 | 4/2019 | Wortz et al. | |
| 10,271,989 B2 | 4/2019 | Haffner et al. | |
| 10,272,176 B2 | 4/2019 | Kahook et al. | |
| 10,285,590 B2 | 5/2019 | Blaauw et al. | |
| 10,285,805 B2 | 5/2019 | de Juan et al. | |
| 10,342,701 B2 | 7/2019 | Rockley | |
| 10,368,759 B2 | 8/2019 | Yu et al. | |
| 10,369,050 B2 | 8/2019 | Camras et al. | |
| 10,383,769 B1 | 8/2019 | Miller | |
| 10,406,030 B2 | 9/2019 | Badawi et al. | |
| 10,426,341 B2 | 10/2019 | Choo et al. | |
| 10,433,950 B2 | 10/2019 | Shadduck | |
| 10,449,085 B2 | 10/2019 | Paulson | |
| 2001/0054774 A1 | 12/2001 | Altmann | |
| 2003/0078487 A1 | 4/2003 | Jeffries et al. | |
| 2003/0225318 A1 | 12/2003 | Montegrande et al. | |
| 2004/0059248 A1 | 3/2004 | Messner et al. | |
| 2004/0254438 A1 | 12/2004 | Chuck et al. | |
| 2005/0119740 A1 | 6/2005 | Esch et al. | |
| 2005/0149139 A1 * | 7/2005 | Plicchi | A61N 1/37229 607/32 |
| 2005/0159660 A1 | 7/2005 | Montegrande et al. | |
| 2005/0182312 A1 | 8/2005 | Bruce et al. | |
| 2006/0135864 A1 | 6/2006 | Westertund et al. | |
| 2006/0136055 A1 | 6/2006 | Michel | |
| 2006/0246112 A1 | 11/2006 | Snyder et al. | |
| 2007/0061393 A1 | 3/2007 | Moore | |
| 2007/0123767 A1 | 5/2007 | Montegrande et al. | |
| 2007/0236213 A1 | 10/2007 | Paden et al. | |
| 2008/0058632 A1 * | 3/2008 | Tai | G01L 9/0072 600/398 |
| 2008/0139947 A1 | 6/2008 | O'Hanlon et al. | |
| 2008/0211320 A1 | 9/2008 | Cook et al. | |
| 2010/0131059 A1 | 5/2010 | Callahan et al. | |
| 2010/0137694 A1 | 6/2010 | Irazoqui et al. | |
| 2010/0179449 A1 | 7/2010 | Chow et al. | |
| 2010/0234717 A1 | 9/2010 | Wismer | |
| 2011/0015733 A1 | 1/2011 | Schnell et al. | |
| 2011/0160609 A1 | 6/2011 | Stone | |
| 2011/0160853 A1 | 6/2011 | Scholten | |
| 2011/0184271 A1 | 7/2011 | Veciana et al. | |
| 2011/0245753 A1 | 10/2011 | Sunalp | |
| 2011/0273287 A1 | 11/2011 | LaLonde et al. | |
| 2012/0197101 A1 | 8/2012 | Telandro | |
| 2012/0226132 A1 | 9/2012 | Wong et al. | |
| 2012/0226133 A1 | 9/2012 | Wong et al. | |
| 2012/0238857 A1 | 9/2012 | Wong et al. | |
| 2013/0041245 A1 | 2/2013 | Cerboni | |
| 2013/0090534 A1 | 4/2013 | Burns et al. | |
| 2013/0109779 A1 | 5/2013 | Argal et al. | |
| 2013/0110540 A1 | 5/2013 | Kimberling | |
| 2013/0150699 A1 | 6/2013 | Ostermeier et al. | |
| 2013/0226293 A1 | 8/2013 | Venkateswaran | |
| 2013/0247644 A1 | 9/2013 | Swoboda et al. | |

(56) References Cited

U.S. PATENT DOCUMENTS

| | | |
|---|---|---|
| 2014/0016087 A1 | 1/2014 | Gupta et al. |
| 2014/0058008 A1 | 2/2014 | Pinchuk et al. |
| 2014/0134607 A1 | 5/2014 | Lin et al. |
| 2014/0148899 A1 | 5/2014 | Fehr et al. |
| 2014/0200424 A1 | 7/2014 | Etzkorn et al. |
| 2014/0243731 A1 | 8/2014 | Rickard et al. |
| 2014/0275923 A1 | 9/2014 | Haffner et al. |
| 2014/0296687 A1 | 10/2014 | Irazoqui et al. |
| 2014/0364717 A1 | 12/2014 | Ostermeier et al. |
| 2014/0371624 A1 | 12/2014 | Ziaie et al. |
| 2015/0057592 A1* | 2/2015 | Gunn ............... A61F 9/00781 604/9 |
| 2015/0094806 A1 | 4/2015 | Scholten |
| 2015/0150510 A1 | 6/2015 | Leonardi et al. |
| 2016/0051143 A1 | 2/2016 | Rickard et al. |
| 2016/0058324 A1 | 3/2016 | Cao |
| 2016/0223842 A1 | 8/2016 | Yun et al. |
| 2016/0235524 A1 | 8/2016 | Wortz et al. |
| 2016/0235587 A1 | 8/2016 | Kahook et al. |
| 2016/0324628 A1 | 11/2016 | Gupta et al. |
| 2017/0020660 A1 | 1/2017 | Hyde et al. |
| 2017/0115511 A1 | 4/2017 | Beaton et al. |
| 2017/0127941 A1 | 5/2017 | Ostermeier et al. |
| 2017/0164831 A1 | 6/2017 | Choo et al. |
| 2017/0209045 A1 | 7/2017 | Choo et al. |
| 2018/0035888 A1 | 2/2018 | Irazoqui et al. |
| 2018/0375382 A1 | 12/2018 | Chappell et al. |
| 2019/0083306 A1 | 3/2019 | Suen et al. |
| 2019/0105199 A1 | 4/2019 | Ahmed et al. |
| 2019/0142632 A1 | 5/2019 | Badawi et al. |
| 2019/0151150 A1 | 5/2019 | Pinchuk et al. |
| 2019/0240069 A1 | 8/2019 | Horvath et al. |
| 2019/0246901 A1 | 8/2019 | Cao et al. |
| 2019/0247232 A1 | 8/2019 | Lynch et al. |
| 2019/0275326 A1 | 9/2019 | Irazoqui et al. |
| 2019/0307769 A1 | 10/2019 | Hughes |
| 2019/0321219 A1 | 10/2019 | Ostermeier et al. |
| 2019/0321226 A1 | 10/2019 | Haffner et al. |
| 2020/0237218 A1 | 7/2020 | Irazoqui et al. |
| 2021/0137379 A1 | 5/2021 | Fehr et al. |
| 2021/0169427 A1 | 6/2021 | Adams et al. |

FOREIGN PATENT DOCUMENTS

| | | |
|---|---|---|
| AU | 2015401840 B2 | 5/2019 |
| AU | 2017345731 B2 | 10/2019 |
| AU | 2018214128 B2 | 10/2019 |
| CN | 201814556 U | 5/2011 |
| CN | 102711593 A | 10/2012 |
| CN | 103037790 A | 4/2013 |
| CN | 103517667 A | 1/2014 |
| CN | 107432733 B | 8/2019 |
| CN | 109157190 B | 10/2019 |
| CN | 110302138 A | 10/2019 |
| EP | 1232723 A1 | 8/2002 |
| EP | 1545303 A2 | 6/2005 |
| EP | 1694205 A1 | 8/2006 |
| EP | 1909697 A2 | 4/2008 |
| EP | 2161004 A1 | 3/2010 |
| EP | 1915115 B1 | 1/2015 |
| EP | 2976042 A1 | 1/2016 |
| EP | 3175820 A1 | 6/2017 |
| EP | 3324890 A1 | 5/2018 |
| EP | 3329884 A1 | 6/2018 |
| EP | 2519141 B1 | 9/2018 |
| EP | 3082570 B1 | 10/2018 |
| EP | 3138474 B1 | 11/2018 |
| EP | 3463226 A2 | 4/2019 |
| EP | 3494959 A2 | 6/2019 |
| EP | 2088976 B1 | 7/2019 |
| EP | 2968668 B1 | 7/2019 |
| EP | 3071091 B1 | 8/2019 |
| EP | 3389559 A4 | 8/2019 |
| EP | 3525736 A1 | 8/2019 |
| EP | 3528747 A1 | 8/2019 |
| HK | 1257538 A | 10/2019 |
| IN | 200606418 P1 | 9/2007 |
| IN | 323231 B | 10/2019 |
| JP | 2013158415 A | 8/2013 |
| JP | 2017018615 A | 1/2017 |
| JP | 6395861 B2 | 9/2018 |
| JP | 2019516451 A | 6/2019 |
| RU | 2017130841 A | 4/2019 |
| WO | WO00/22460 A1 | 4/2000 |
| WO | WO2002/019949 A2 | 3/2002 |
| WO | WO2006/067638 A2 | 6/2006 |
| WO | WO2008/134573 A1 | 11/2008 |
| WO | WO2009/137085 A2 | 11/2009 |
| WO | WO2010/093873 A2 | 8/2010 |
| WO | 2013090886 A1 | 6/2013 |
| WO | 2016004262 A1 | 1/2016 |
| WO | WO2016/033270 A1 | 3/2016 |
| WO | WO2016/160456 A1 | 10/2016 |
| WO | WO2017/223387 A1 | 12/2017 |
| WO | WO2018/031982 A1 | 2/2018 |
| WO | 2019164940 A1 | 8/2019 |
| WO | 2019191748 A1 | 10/2019 |
| WO | 2019216945 A1 | 11/2019 |
| WO | 2020023036 A1 | 1/2020 |
| WO | 2020046299 A1 | 3/2020 |
| WO | 2020081072 A1 | 4/2020 |
| WO | 2020160262 A1 | 8/2020 |
| WO | 2020236139 A1 | 11/2020 |

OTHER PUBLICATIONS

Chen et al., "Implantable parylene-based wireless intraocular pressure sensor." 2008 IEEE 21st International Conference on Micro Electro Mechanical Systems. IEEE, 2008. 4 pages.

Chen et al., "Microfabricated implantable parylene-based wireless passive intraocular pressure sensors." Journal of Microelectromechanical Systems 17.6 (2008): 1342-1351.

Ha et al., "Polymer-based miniature flexible capacitive pressure sensor for intraocular pressure (IOP) monitoring inside a mouse eye." Biomedical microdevices 14.1 (2012): 207-215.

Haque et al., "An intraocular pressure sensor based on a glass reflow process." Solid-State Sensors, Actuators, and Microsystems Workshop. Hilton Head Island, 2010. 4 pages.

Hastings et al., "An Implantable, All-Optical Sensor for Intraocular Pressure Monitoring." Investigative Ophthalmology & Visual Science 53.14 (2012): 5039-5039. 1 page.

Kim et al., "Preliminary study on implantable inductive-type sensor for continuous monitoring of intraocular pressure." Clinical & experimental ophthalmology 43.9 (2015): 830-837.

Koley et al., "Miniaturized implantable pressure and oxygen sensors based on polydimethylsiloxane thin films." Materials Science and Engineering: C 29.3 (2009): 685-690.

Piffaretti et al., "Rollable and implantable intraocular pressure sensor for the continuous adaptive management of glaucoma." (2013): 3198-3201.

Yu et al., "Chronically implanted pressure sensors: challenges and state of the field." Sensors 14.11 (2014): 20620-20644.

Extended European Search Report in European Patent Application No. 17807410.0 dated Jun. 26, 2020, 10 pages.

International Search Report and Written Opinion in International Patent Application No. PCT/US2017/035247 dated Aug. 10, 2017, 10 pages.

Partial Supplementary European Search in European Patent Application No. 17807410.0 dated Mar. 12, 2020, 12 pages.

Eldred et al.; The lens as a model for fibrotic disease; Philosophical Transactions of the Royal Society B: Biological Sciences; 366(1568); pp. 1301-1319; Apr. 27, 2011.

Farandos et al.; Contact lens sensors in ocular diagnostics; Advanced Healthcare Materials; 4(6); pp. 792-810; Apr. 2015.

Gharib et al.; Liposomes incorporating cyclodextrin-drug complexes: Current state of knowledge; Carbohydrate Polymers, vol. 129; pp. 175-186; Sep. 20, 2015.

(56) References Cited

OTHER PUBLICATIONS

Hiryama et al.; Permeation properties to CO2 and N2 of poly(ethylene oxide)-containing and crosslinked polymer films; Journal of Membrane Science; 160(1); pp. 87-99; Jul. 15, 1999.
Leonardi et al.; Wireless contact lens sensor for intraocular pressure monitoring: assessment on enucleated pig eyes; Acta Opthalmology; 87(4); pp. 433-437; Jun. 2009.
Pintwalla; Development of an in-vitro model to assess wound healing response and biocompatibility of intraocular biomaterials; Masters Thesis; University of Waterloo; 120 pages; Oct. 21, 2014.
Wallace et al.; A tissue sealant based on reactive multifunctional polyethylene glycol; Journal of Biomedical Materials Research: An Official Journal of the Society for Biomaterials, The Japanese Society for Biomaterials, and the Australian Society for Biomaterials and the Korean Society for Biomaterials; 58(5); pp. 545-555; (year of pub. sufficiently earlier than effective US filing date and any foreign priority date) 2001.
Araci et al.; An implantable microfluidic device for self-monitoring of intraocular pressure; Nature Medicine; 20(9); pp. 1074-1078; Sep. 2014.
Chen et al.; Implantable parylene-based wireless intraocular pressure sensor; IEEE 21st Intl. Conf. on Micro Electro Mechanical Systems (MEMS 2008); pp. 58-61; Jan. 13, 2008.
Chen et al.; Microfabricated implantable Parylene-based wireless passive intraocular pressure sensors; J. Microelectromech. Syst.; 17(6); pp. 1342-1351; Dec. 2008.
Ha et al.; Polymer-based miniature flexible capacitive pressure sensor for intraocular pressure (IOP) monitoring inside a mouse eye; Biomed Microdevices; 14(1); pp. 207-215; Feb. 1, 2012.
Hafezi et al.; An ingestible sensor for measuring medical adherence; IEEE Trans on Biomed Eng; 62(1); pp. 99-109; Jan. 2015.
Haque et al.; An intra-ocular pressure sensor based on a glass reflow process; Solid-State Sensors, Actuators, and Microsystems Workshop; Hilton Head Island, South Carolina; Jun. 6-10, 2010.
Hastings et al.; An implantable, all-optical sensor for intraocular pressure monitoring; Investigative Ophthalmology and Visual Science; 53(14); p. 5039; Mar. 26, 2012.
Hogg et al.; Protective multilayer packaging for long-term implantable medical devices; Surface and Coatings Technology; 255; pp. 124-129; Sep. 25, 2014.
Kim et al.; Preliminary study on implantable inductive-type sensor for continuous monitoring of intraocular pressure; Clinical and Experimental Ophthalmology; 43(9); pp. 830-837; Dec. 2015.
Koley et al.; Miniaturized implantable pressure and oxygen sensors based on polydimethylsiloxane thin films; Mater. Sci. Eng.: C; 29(3); pp. 685-690; Apr. 30, 2009.
Kuno et al.; Biodegradable intraocular therapies for retinal disorders; Drugs and Aging; 27(2); pp. 117-134; Feb. 1, 2010.
Kuno et al.; Recent advances in ocular drug delivery systems; Polymers; 3(1); pp. 193-221; Jan. 6, 2011.
Ludwig et al.; Health-enabling technologies for the elderly—An overview of services based on a literature review; Comput Methods Programs Biomed; 106(2); pp. 70-78; May 1, 2012.
Piffaretti et al.; Rollable and implantable intraocular pressure sensor for the continuous adaptive management of glaucoma; Eng. in Med. and Biol. Soc. (EMBC), 2013 35th Annual Int. Conf. of the IEEE; pp. 3198-3201; Jul. 3, 2013.
Redmond et al.; What does big data mean for wearable sensor systems?; Contribution of the IMIA wearable sensors in Healthcare WG; Yearbook of Medical Informatics; 9(1); pp. 135-142; Aug. 15, 2014.
Varel et al.; A wireless intraocular pressure monitoring device with a solder-filled microchannel antenna; J. Micromech. Microeng.; 24(4); pp. 1-8; Mar. 13, 2014.
Yu et al.; Chronically implanted pressure sensors: challenges and state of the field; Sensors; 14(11); pp. 20620-20644; Nov. 2014.
Kompella et al.; Delivery of celecoxib for treating diseases of the eye: influence of pigment and diabetes; Expert opinion on Drug Delivery; 7(5); pp. 631-645; 24 pages (Author Manuscript); May 2010.
Siatiri et al.; Intracameral tissue plasminogen activator to prevent severe fibrinous effusion after congenital cataract surgery; British Journal of Ophthalmology; 89(11); pp. 1458-1461; doi: 10.1136/bjo.2005.071407; Nov. 2005.
Stanke et al.; Suppression of TGF-Beta pathway by pirfenidone decreases extracellular matrix deposition in ocular fibroblasts in vitro; Plos One; 12(2); 20 pages; DOI: 10.1371; Feb. 23, 2017.

\* cited by examiner

DIMENSIONS IN mm

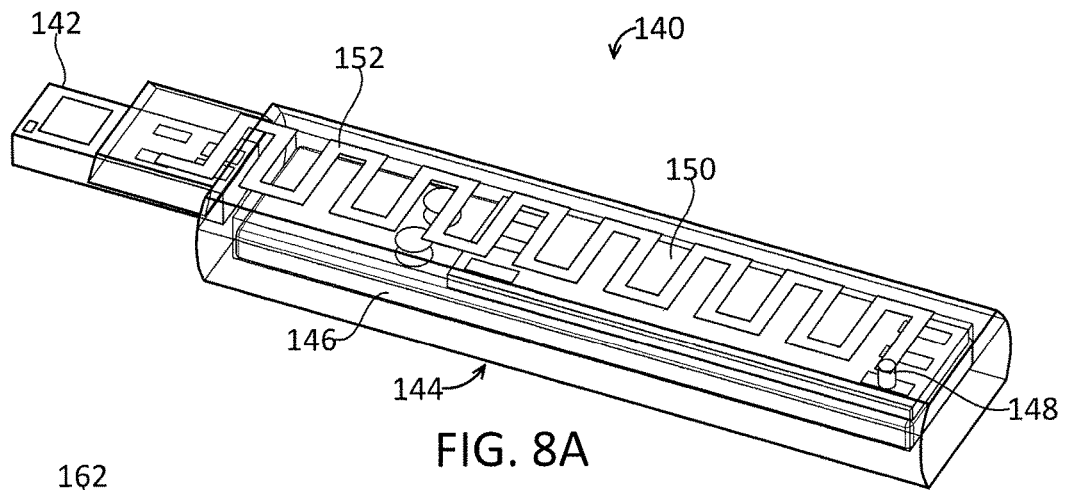
FIG. 8A
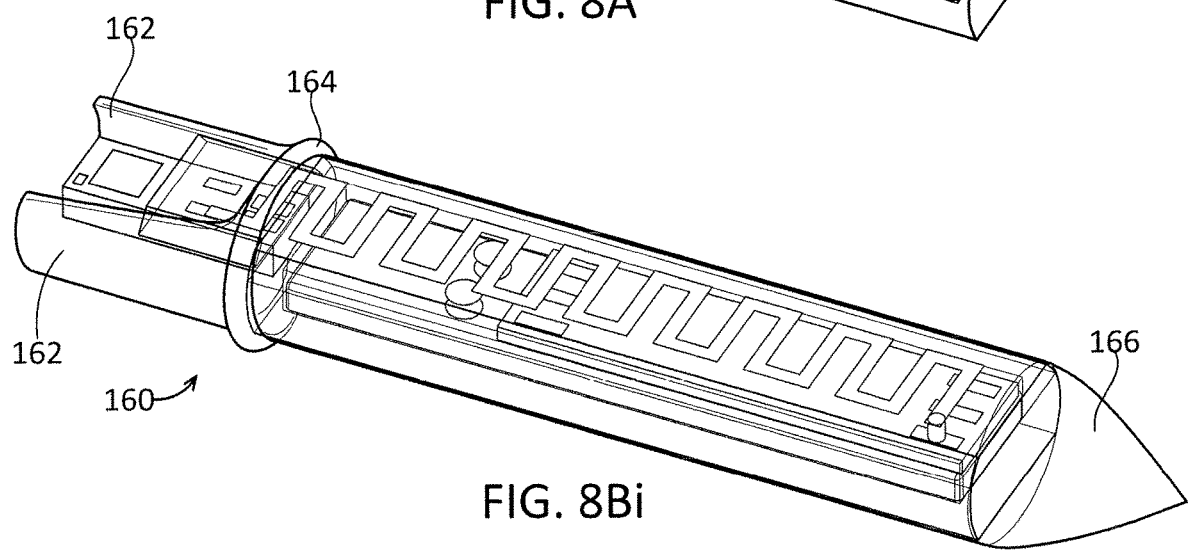
FIG. 8Bi
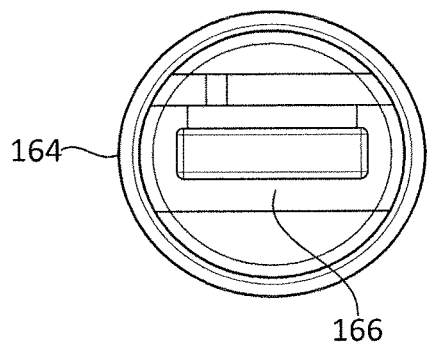
FIG. 8Bii

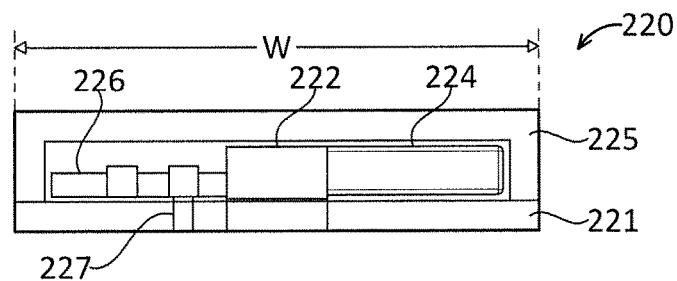
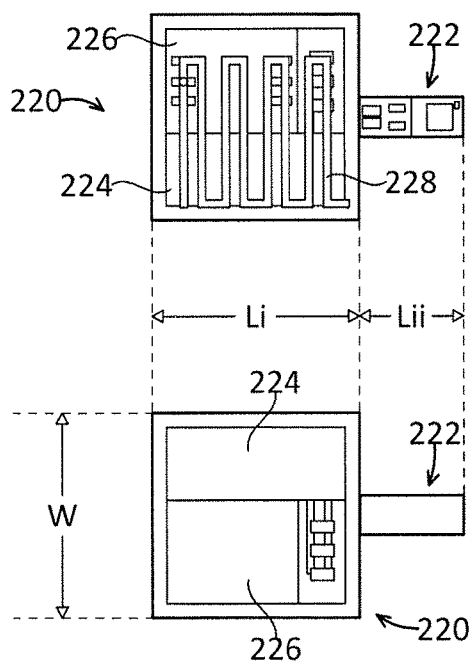
FIG. 12D
BOTTOM VIEW
FIG. 12C
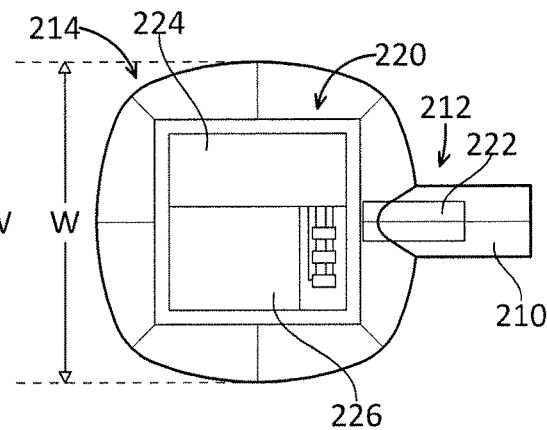
FIG. 12E
FIG. 12F
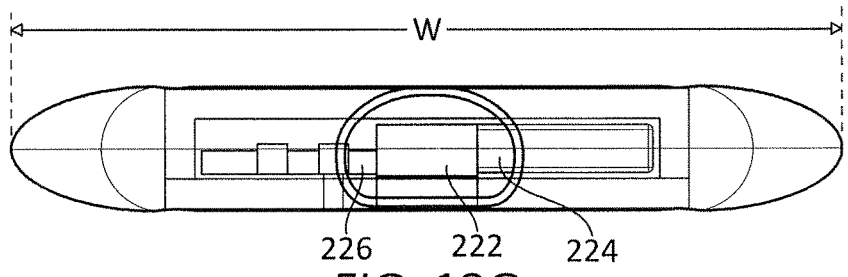
FIG. 12G

AN AMPHIPHILIC COATING WITH INFUSED OR WEAKLY BONDED ANTICOAGULANTS

GREATER NUMBER DENSITY OF HYDROPHILIC GROUPS AT THE SURFACE

IMPLANTABLE INTRAOCULAR PRESSURE SENSORS AND METHODS OF USE

CROSS REFERENCE TO RELATED APPLICATIONS

This application is a national-phase application, under 35 U.S.C. 371, of International Application No. PCT/US2017/035247, filed on May 31, 2017, which in turn claims priority to U.S. Provisional Application No. 62/343,593, filed May 31, 2016, the disclosure of each of which is incorporated by reference herein.

This disclosure incorporates the following publications by reference herein: U.S. Pat. Nos. 8,475,374; 9,078,613; US 2010/0137694; US 2010/0179449; and US 2014/0296687.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Glaucoma is second only to cataract as a leading cause of global blindness and is the leading cause of irreversible visual loss. Worldwide, there were 60.5 million people with open angle glaucoma and angle closure glaucoma in 2010, projected to increase to 79.6 million by 2020, and of these, 74% will have OAG. (Quigley and Broman, in Br J Ophthalmol. 2006; 90(3), pp 262-267). Of those with ACG, it is predicted that 70% will be women and 87% will be Asian. Open-angle glaucoma affects more than 2 million individuals in the United States. Owing to the rapid aging of the US population, this number will increase to more than 3 million by 2020, and approximately a total of 4 million glaucoma cases. Bilateral blindness from glaucoma is projected to affect greater than 11 million by 2020 globally. Risk factors for open-angle glaucoma include increased age, African ethnicity, family history, increased intraocular pressure, myopia, and decreased corneal thickness. Risk factors for angle closure glaucoma include Inuit and Asian ethnicity, hyperopia, female sex, shallow anterior chamber, short axial length, small corneal diameter, steep corneal curvature, shallow limbal chamber depth, and thick, relatively anteriorly positioned lens.

Elevated intraocular pressure ("IOP") is the most important known risk factor for the development of POAG, and its reduction remains the only clearly proven treatment. Several studies have confirmed that reduction of IOP at any point along the spectrum of disease severity reduces progression (Early Manifest Glaucoma Treatment Trial to Advanced Glaucoma Intervention Study). Also, IOP reduction reduces the development of POAG in patients with ocular hypertension (OHT) and reduces progression in patients with glaucoma despite normal IOP, as seen in the Collaborative Normal Tension Glaucoma Study. The normal IOP for 95% of Caucasians is within the range of 10-21 mm Hg. While increased IOP is a strong risk factor for the development of glaucoma, it must be remembered that many people with glaucoma have untreated IOPs of 21 mm Hg or less. In general, it is estimated that approximately 50% of POAG is of the normal tension variety. However, studies have found a wide range in the prevalence of normal tension glaucoma among individuals with OAG. For example, normal tension glaucoma was diagnosed in 1/3 of the OAG patients in the Barbados Eye Studies, and 85% of the individuals with OAG in a Chinese population. At this time, the risk associated with long-term fluctuation of IOP over months to years remains controversial. The EGPS and Early Manifest Glaucoma Treatment Trial found that long-term IOP fluctuations were not associated with progression of glaucoma, while the AGIS study found an increased risk of glaucoma progression with increased long-term IOP fluctuation, especially in patients with low IOP.

Currently, IOP reduction remains the only treatment option for glaucoma, with options depending on many factors such as the type of glaucoma. Current monitoring of IOP occurs in the offices of a vision care practitioner, typically an ophthalmologist, ranging from once a year to once every 3-6 months, once glaucoma is diagnosed. It is known that IOP varies over a wide range in individuals, including a diurnal fluctuation, longer term variations and occurrence of spikes in IOP, therefore a single measurement cannot provide adequate data to diagnose an elevated IOP, requiring prescription of pressure regulating or pressure reducing medication. Treatment options for reduction of IOP include medical therapy, such as beta blockers, alpha agonists, miotics, carbonic anhydrase inhibitors, and prostaglandin analogues, administered as eyedrops, up to 4 times a day; laser treatment, such as argon laser trabeculoplasty (ALT), selective laser trabeculoplasty (SLT), neodymium-doped yttrium aluminum garnet (Nd:YAG) laser iridotomy, diode laser cycloablation, and laser iridoplasty; surgical procedures including iris procedures (e.g., peripheral iridectomy), angle procedures (e.g., goniotomy and trabeculotomy), filtration procedures (e.g., trabeculectomy) and non-penetrating filtration procedures (e.g., deep sclerectomy and viscocanalostomy); and drainage shunts including episcleral implants (e.g., Molteno, Baerveldt, and Ahmed) or minishunts (e.g., *ExPress Mini Shunt and iStent*).

Prevalence of glaucoma in white (A) and black and Hispanic (B) subjects is shown in BES, Baltimore Eye Survey, Baltimore, Md.; BDES, Beaver Dam Eye Study, Beaver Dam, Wis.; BMES, Blue Mountain Eye Study, Sydney, NSW; Melbourne VIP, Melbourne Visual Impairment Project, Melbourne, VIC; RS, Rotterdam Study, Rotterdam, the Netherlands; Barbados, Barbados Eye Study, Barbados, West Indies; KEP, Kongwa Eye Project, Tanzania; and Proyecto VER, Vision Evaluation Research, Nogales and Tucson, AZ. "Eye Diseases Prevalence Research Group (2004) Prevalence of open-angle glaucoma among adults in the United States.", *Arch Ophthalmol* 122:532-538.

A substantial majority of glaucoma patients are treated by medication to control IOP, sometimes over three decades. Patients treated surgically or using laser treatment may also be administered medication. Lack of compliance of patients to long term medication protocols is exacerbated by advancing age and lack of positive concrete immediate incentives.

Monitoring compliance—continuous monitoring of IOP replaces the standard practice of monitoring IOP episodically, hence provides a more accurate and detailed account of patient compliance, enabling the caregiver to take steps to take additional steps to enhance compliance if required.

Monitoring efficacy of prescribed treatment—continuous IOP data following a change in treatment modality or protocol provides the caregiver with a prompt feedback on the efficacy of the change in treatment and thereby supports a better outcome.

Post market monitoring of approved glaucoma treatments—newly approved glaucoma treatments may require post market monitoring by health care agencies in order to monitor safety and efficacy on the targeted patient population Data from continuous monitoring of IOP may be submitted by manufacturers of newly approved drugs or devices to meet this requirement.

Clinical research on efficacy of novel glaucoma treatments—data recorded may be used by clinical researchers to monitor efficacy and may be submitted to regulatory authorities for prompt approval, if the results so warrant.

The references below describe some earlier concepts related to monitoring intraocular pressure.

1. "An implantable microfluidic device for self-monitoring of intraocular pressure", by Mandel, Quake, Su and Araci, in *Nature Medicine* 20, 1074-1078 (2014). Three images of a microfluidic intraocular sensor are shown in this reference. The sensor comprises a 50×50 µm$^2$ cross-section channel connected to the eye fluid on one side and to a 0.5 mm×2.0 mm×0.3 mm volume reservoir ($V_{reservoir}$) on the other.

2. "Implantable parylene-based wireless intraocular pressure sensor", by Chen, Rodger, Saati, Humayun and Tai in IEEE 21$^{st}$ International Conference on Micro Electro Mechanical Systems, 2008. MEMS 2008. This paper presents an implantable, wireless, passive pressure sensor for ophthalmic applications. Two sensor designs incorporating surface-micro-machined variable capacitor and variable capacitor/inductor are implemented to realize the pressure sensitive components. The sensor is monolithically microfabricated using parylene as a biocompatible structural material in a suitable form factor for increased ease of intraocular implantation. Pressure responses of the microsensor are characterized on-chip to demonstrate its high pressure sensitivity (>7000 ppm/mmHg) with mmHg level resolution. An in vivo animal study verifies the biostability of the sensor implant in the intraocular environment after more than 150 days.

3. "Rollable and implantable intraocular pressure sensor for the continuous adaptive management of glaucoma", Piffaretti, Barrettino, Orsatti, Leoni, Stegmaier, in Conference Proceedings IEEE Eng Med Biol Soc, 2013;2013: 3198-201. doi: 10.1109/EMBC.2013.6610221.

4. "Implantable microsensor, telemetrically powered and read out by patient hand-held device", by Implandata Ophthalmic Products GmbH Kokenstrasse 5 30159 Hannover Germany, 2014. The Eyemate® by Implandata Ophthalmic Products GmbH is also an example.

5. "Preliminary study on implantable inductive-type sensor for continuous monitoring of intraocular pressure", by Kim Y W, Kim M J, Park, Jeoung, Kim S H, Jang, Lee, Kim J H, Lee, and Kang in *Clinical & Experimental Ophthalmology*, 43(9), pp 830-837, 2015.

6. "An intra-ocular pressure sensor based on a glass reflow process", by Haque and Wise in *Solid-State Sensors, Actuators, and Microsystems Workshop, Hilton Head Island, S.C., Jun.* 6-10, 2010.

7. Some earlier approaches used a capacitive-based membrane pressure sensor. For example, a diaphragm can deflect under pressure, changing the effective distance between two parallel plates, and thus increasing the measured capacitance across the plates. An example is "Miniaturized implantable pressure and oxygen sensors based on polydimethylsiloxane thin films", Koley, Liu, Nomani, Yim, Wen, Hsia: in *Mater. Sci. Eng. C* 2009, 29, 685-690.

8. "Microfabricated implantable Parylene-based wireless passive intraocular pressure sensors", by Chen, Rodger, Saati, Humayun, Tai: *J. Microelectromech. Syst.* 2008, 17, 1342-1351.

9. "An Implantable, All-Optical Sensor for Intraocular Pressure Monitoring", by Hastings, Deokule, Britt and Brockman in *Investigative Ophthalmology & Visual Science*, 2012. Vol.53, pp 5039. A simplified approach to IOP monitoring based on a near infrared (NIR) image of an implanted micromechanical sensor is presented. The sensor chip contains one or more vacuum reference cavities formed by a flexible membrane, a rigid substrate, and a thin spacer. Both substrate and membrane partially reflect light to form an interference pattern of concentric rings. These rings shift radially as the membrane deflects in response to pressure changes. IOP is measured by analyzing a narrow-band NIR image of the pattern.

10. "Chronically Implanted Pressure Sensors: Challenges and State of the Field", A Review by Yu, Kim and Meng, in *Sensors* 2014, 14, 20620-20644; doi:10.3390/s141120620.

12. "Polymer-based miniature flexible capacitive pressure sensor for intraocular pressure (IOP) monitoring inside a mouse eye", by Ha, de Vries, John, Irazoqui, and Chappell in *Biomed Microdevices* (2012) 14:207-215, DOI 10.1007/s10544-011-9598-3.

13. "Intra-ocular pressure sensor", U.S. Pat. No. 8,475,374 B2, by Irazoqui, Chow, Chappelle, Yang, and Ziaie, 2013.

SUMMARY OF THE DISCLOSURE

One aspect of the disclosure is a hermetically sealed implantable intraocular pressure sensor assembly adapted to wirelessly communicate with an external device. The assembly can include a hermetically sealed housing, the hermetically sealed housing can include therein: an antenna in electrical communication with a rechargeable power source, the rechargeable power source in electrical communication with an ASIC, and the ASIC in electrical communication with a pressure sensor.

In some embodiments, the antenna is part of a first circuit adapted to supply power to the rechargeable power source, and the antenna is also part of a second circuit adapted to transmit data to the external device.

In some embodiments, the assembly further comprises a flexible circuit, the flexible circuit in electrical communication with the pressure sensor and the ASIC. The flexible circuit can be in electrical communication with the antenna and the power source.

In some embodiments, the assembly further comprises a casing comprising a titanium layer. The titanium layer can be coated with an electrically insulating ceramic layer, wherein said ceramic layer has lattice constants that match those of Titanium. The titanium layer can be coated with a hydrogel coating, wherein said hydrogel layer has a gradient in cross-link density. The hydrogel layer can have a gradient in number density of hydroxyl groups, said gradient being in the opposite direction of the gradient in cross-link density. The hydrogel layer can be impregnated with an anticlotting agent. The hydrogel layer can be impregnated with an anti-inflammatory agent. An outer surface of the hydrogel coating can be textured to stimulate a controlled fibrotic response. The coating can be infused with at least one of an anti-inflammatory agent and an anticlotting agent. The coating can be chemically bonded to medicaments that are slowly and sustainably released into the eye over a period of not less than 10 days. The textured surface can include a plurality of depressions, each of which have a height between 5 microns and 15 microns, such as 7.5 microns and 12.5 microns, such as 10 microns.

In some embodiments, the pressure sensor comprises a hermetically sealed module comprising an inert fluid situated inside the module. The hermetic seal encasing said pressure sensor can include a Titanium foil of thickness in the range of 5-25 microns, the foil being undulated to enhance its surface area and resistance to mechanical stress. The sensor can comprise a piezoelectric sensing element wherein said inert fluid of claim 12 transmits hydrostatic pressure to said sensing element through said Titanium foil. The sensor can comprise a capacitative sensing element wherein said inert fluid of claim 12 transmits hydrostatic pressure to said sensing element through said Titanium foil. The sensor can have dimensions of length 0.2 mm to 1.5 mm in length, 0.2 mm to 0.7 mm in width and 0.1 mm to 0.7 mm in thickness.

In some embodiments, the antenna has a space filling design, wherein the antenna is connected to an electrical circuit that can be adjusted for its electrical impedance as a function of its resistive load. The antenna can be disposed on a ceramic substrate situated inside a Titanium casing, wherein said antenna assembly being of thickness in the range 100-500 microns. The circuit comprising the antenna can have a Q factor in the range of 10-50 under use conditions. The antenna can be comprised of vacuum deposited metal filaments on a ceramic substrate. The antenna can provide both data transfer and energy transfer functions. The antenna can comprise a conductive length of no less than 15 mm and no more than 100 millimeters. The antenna can transmit electromagnetic energy at a frequency that is not harmful to the human body.

In some embodiments, the ASIC comprises a microelectronic circuit comprising a microcontroller, a flash memory, a non-volatile memory and a logic circuit. The logic circuit can comprise power management and data management modules. The ASIC comprises a microelectronic circuit wherein said microelectronic circuit comprises conductive connectors of width in the range 36-360 nanometers.

In some embodiments, the implantable assembly has a length not greater than 4.8 mm (e.g., not greater than 4.5 mm), a height not greater than 1.5 mm, and a width not greater than 1.5 mm.

In some embodiments, the pressure sensor is disposed inside of a fluid filled chamber. The fluid filled chamber can include a flexible membrane adapted to transmit pressure from the external environment to a fluid within the fluid filled chamber. The flexible membrane can be 5-20 microns thick, such as 7-17 microns thick. The flexible membrane can be selected from the group consisting of film forming materials that provide a barrier to gas diffusion, including diffusion of air and water, for example only, Titanium, Parylene, polyimides such as Kapton, polyaromaitcs such as polyphenylene, etc.

In some embodiments, the pressure sensor is adapted to sense intraocular pressure more than once every 12 hours and no more than once every 10 milliseconds, and wherein the ASIC is adapted to facilitate the storage of pressure data more than once every 12 hours and no more than once every 10 milliseconds.

In some embodiments, the assembly further comprises an external device in wireless communication with the implantable assembly. The external device can have a communication component that is adapted to transmit a wireless signal to the implantable assembly indicating its readiness to receive data from the implantable assembly and provide wireless power to the implantable assembly, and wherein the ASIC is adapted to acknowledge the transmitted wireless signal with one of at least two different signals, indicating its readiness to transmit or receive data and its readiness to receive wireless power.

In some embodiments, the ASIC has a communication component that is adapted to transmit pressure data from the implantable assembly to the external device, wherein the external device has a communication component that is adapted to receive the transmitted pressure data, wherein the ASIC is adapted to transmit the pressure data upon receiving a trigger signal from the external device and after acknowledging the receipt of the trigger signal.

In some embodiments, the ASIC has a communication component that is adapted to transmit pressure data from the implantable assembly to the external device, wherein the external device has a communication component that is adapted to receive the transmitted pressure data, wherein the ASIC is adapted to transmit the pressure data upon receipt of an acknowledgment signal from the external device of receipt of a trigger signal from the implantable assembly.

BRIEF DESCRIPTION OF THE DRAWINGS

FIGS. 12A-12G illustrate an exemplary implant that has a general square configuration.

DETAILED DESCRIPTION

This disclosure relates generally to intraocular pressure sensors, intraocular pressure sensing, and systems for using, and the use of, the sensed pressure or information indicative of the sensed pressure. The sensors and methods herein may also, however, be used in sensing pressure in areas near or outside of the eye. For example, sensors and methods of use herein may be used in episcleral, cardiac or neural applications, including the brain.

Some aspects of the disclosure include implantable intraocular pressure sensors that are adapted, configured, and sized to be positioned and stabilized within the eye and communicate, optionally wirelessly, with one or more devices positioned within or outside the eye. A wireless intraocular pressure sensor may be referred to herein as a "WIPS," and an implantable device may be referred to herein an implant, or an implantable portion of a system.

Some of the devices, systems, and methods of use herein provide an exemplary advantage that they can sense intraocular pressure more frequently than possible with traditional tonometry and office visits, and can thus provide more frequent information regarding the change in pressure of an eye. For example, some devices herein are adapted to sense intraocular pressure continuously, substantially continuously, or periodically (regular intervals or non-regular intervals) when implanted in an eye.

An autonomous, implantable sensor is preferred in order to provide monitoring, optionally continuous, of IOP, in order to avoid relying on the patient to perform monitoring and management tasks that can be quite onerous for a sensor continuously recording IOP data. An autonomous implanted sensor can include an electrically operated sensor that measures pressure of the aqueous humor and converts it to an electrical signal, an internal power source, optionally provided by a rechargeable battery, an electrical controller such as a microcontroller or an ASIC to manage the electronic system, a memory unit comprising volatile and/or non-volatile memory, and a wireless link in order to, optionally, receive power wirelessly, download data to an external device, and optionally a data uplink to allow reprogramming capability. The data can be downloaded into a smart phone or a tablet that serves a data uplink to a caregiver's computer via a wireless or cabled network. Power can be provided from an external charging unit that has its own power management integrated circuit (PMIC), and may also have a wireless data transfer capability, and thus can function as an interface between the implanted device and the smart phone or a tablet.

Figure 1:
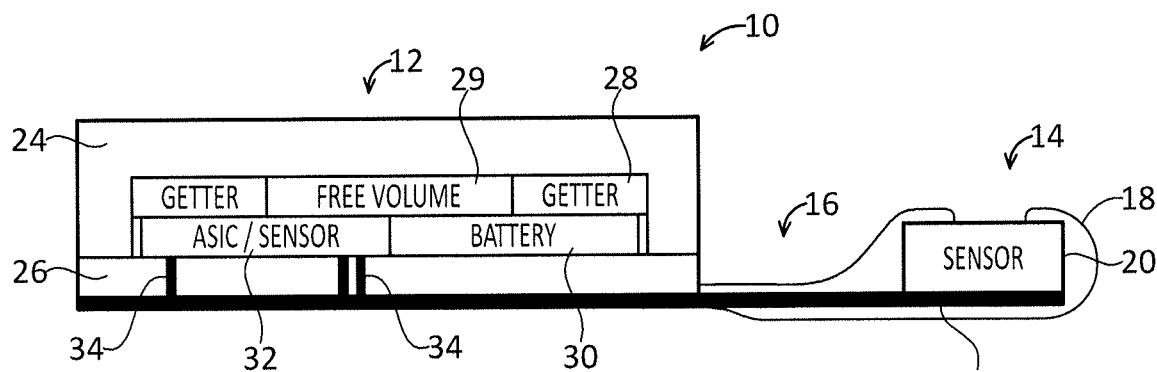
FIG. 1 schematically illustrates exemplary components of an exemplary implant.

FIGS. 1-17 and 21 illustrate aspects of merely exemplary implants that can be used with the systems and methods of use herein. FIG. 1 schematically illustrates exemplary components of an exemplary implant 10. Any of the implants herein can include a pressure sensor, a housing that hermetically surrounds an ASIC and battery, and a flexible substrate/connector to which the housing and pressure sensor are secured. The flexible substrate/connector can include an electrical connection to the pressure sensor and antenna.

One of the challenges when designing a wireless implant that includes an intraocular pressure sensor is conceiving of a way to incorporate components into a hermetically sealed device that includes a pressure sensor, antenna, power source, and controller, wherein the device can be implanted securely and safely into the eye, and still provide and communicate sensed data or information indicative of intraocular pressure to an external device.

Exemplary implant 10 includes first portion 12 secured to sensor portion 14 via connector portion 16. Substrate 22 extends between sensor portion 14 and first portion 12. Sensor portion 14 includes at least one pressure sensor 20 disposed within an encapsulation 18, optionally silicone or other similar material. Sensor 20 is in operable pressure communication with the external environment, such that external pressures can be transmitted to pressure sensor 20. This can be, for example, via an area of sensor portion 14 (e.g., encapsulation 18) that does not extend over the pressure sensor 18 as shown.

Substrate 22 carries electronics that allow signals from sensor 18 to be communicated to first portion 12. Data or signals indicative of sensed data can be communicated via sensor portion 14 to controller 32 with sealed vias 32 and 34, which is this exemplary embodiment comprises an ASIC. First portion 12 includes top casing 24 and bottom casing 26, which together form a hermetic seal that houses components therein. Top and bottom casings can be, in some embodiments, rigid glass material or titanium. The first portion also includes battery 30, and can also include water getter 28, and free volume 29.

Figure 2:
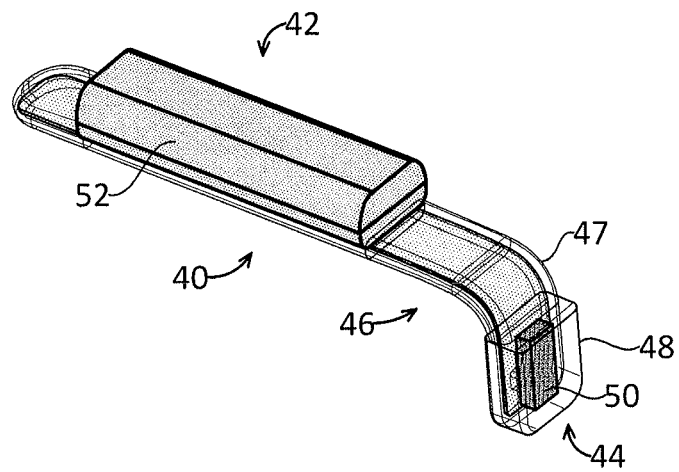
FIG. 2 illustrate an exemplary implant with a flexible connector portion.
Figure 3:
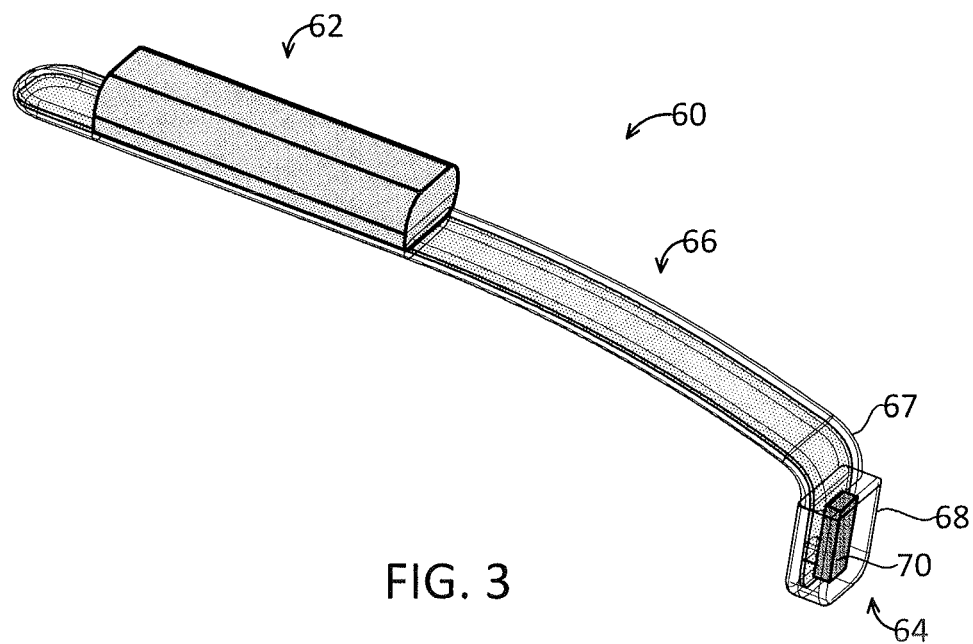
FIG. 3 illustrate an exemplary implant with a longer flexible connector portion than the exemplary implant in FIG. 2.

FIGS. 2 and 3 illustrate substantially the same implants 40 and 60, with implant 60 having a longer flexible connector portion 66 than implant 42's connector portion 46. Both implants include a first portion 42/62, respectively, secured to the sensor portion via the flexible connector portion. Both implants also include sensor portion 44 and 64 respectively, which include sensors 50 and 70, respectively. First portions 42 and 62 can include any of the components of the implants herein, such as a power source, controller (e.g., ASIC), memory, water getter, etc.

Connector portions 46 and 66 each also include bend regions 47/67, respectively. Bend regions 47 and 67 are closer to sensor portions 44/64 than first portions 42/62. The bend regions are optional, as other embodiments do not necessarily need to include them.

In some embodiments the implant has an overall length such that the pressure sensor can be positioned in the anterior chamber and the housing is positioned in the suprachoroidal space of an average adult. The flexible substrate can include a bend, or region of increased curvature, as shown in some embodiments herein.

Figure 4A:
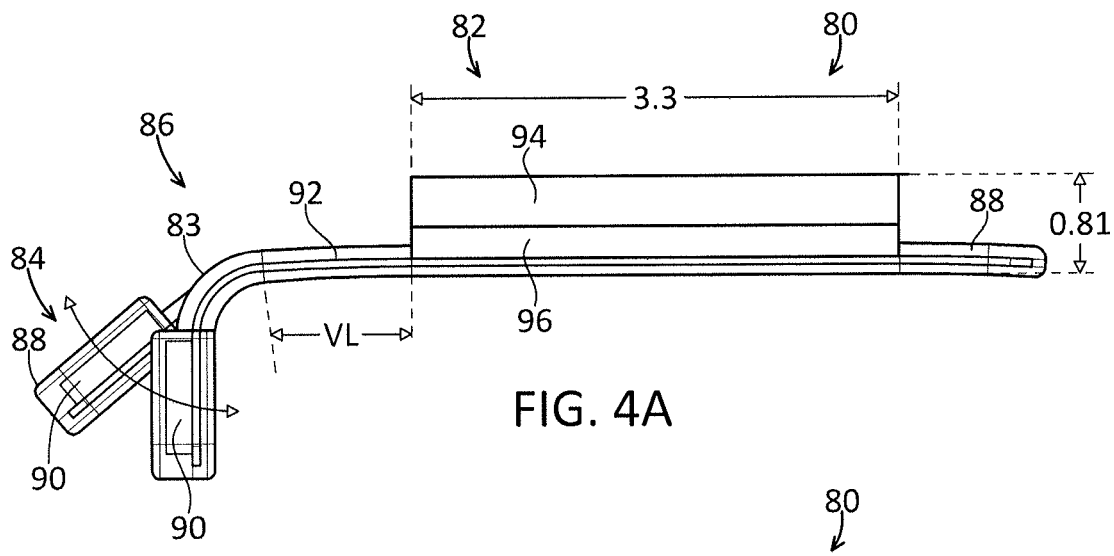
FIGS. 4A, 4B and 4C illustrates some exemplary views of an exemplary implant, which can be the same as or similar to the exemplary implant FIG. 2.
Figure 4B:
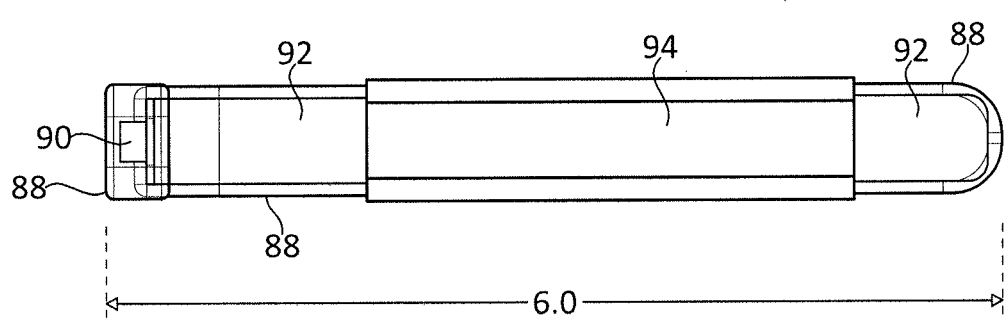
Figure 4C:
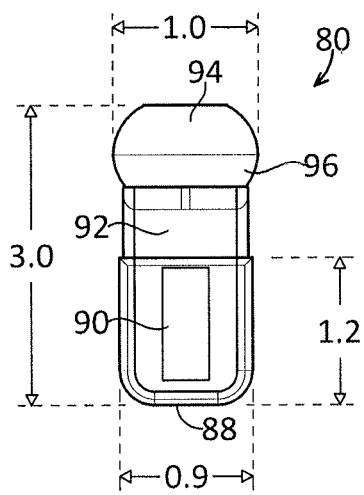

FIGS. 4A-4C illustrates some exemplary views of the exemplary implant, which can be the same or similar as implant 40 from FIG. 2, and which illustrate exemplary specific dimensions. The implants herein can be configured and sized to fit within a 0.6 mm to 2.0 mm outer diameter, and in particular a 1.0 mm outer diameter lumen, such as a needle. The dimensions shown in the FIGS. 4A-4C are illustrative and not limiting.

Implant 80 includes first portion 82, sensor portion 84, and connector portion 86. A casing or encapsulation 88 extends around sensor portion 84, connector portion 86, and along the bottom of first portion 82. Sensor portion 84 includes pressure sensor 90 disposed within encapsulation 88, but encapsulation can have a window therein so sensor 90 is in pressure communication with the environment. The first portion 82 can include any of the electronics and other components (battery, memory, antenna, etc.) described herein. Substrate or base layer 92 extends from the sensor portion 84 to the first portion 82, and carries electronics (e.g., flex circuits printed on a substrate) that electrically couple sensor 90 and electronics within first portion 82. Substrate 92 also comprises an antenna adapted for wireless data and power transfer.

As shown in the side view of FIG. 4A, the exemplary length of the housing of first portion 82 is 3.3 mm, whereas the height of the housing and encapsulation is 0.81 mm. As shown in the top view of FIG. 4B, the overall length of the implant is 6.0 mm. As shown in the front view of FIG. 4C, the overall width is 1.0 mm, while the exemplary sensor portion (including encapsulation) is 0.9 mm wide and 1.2 mm tall. The height of the overall device 3.0 mm.

FIG. 4A illustrate that connector portion 86 has a bend 83 along its length closer to the sensor portion 84 than first portion 82, and is flexible along its length, and the flexibility of connector portion 86 allows sensing portion 84 to move relative to first portion 82. In an at-rest, or nondeformed configuration, the bend 83 in connector portion 86 is such that connector portion 86 and sensor portion 84 have axes that are orthogonal to each other. Bend 83 can have a single radius of curvature of can have a varying radius of curvature.

Encapsulation 83 can be a deformable material such as silicone (compatible with off-the-shelf piezo and capacitive MEMS sensors). Top and bottom portions 94 and 96 can be glass or titanium, as is set forth herein.

The flexible electronics on the substrate can include the contacts for the sensor and the antenna. Incorporating an antenna into the flexible substrate is one way of incorporating an antenna into a compact implantable device while still allowing for data and power transmission.

Figure 5A:
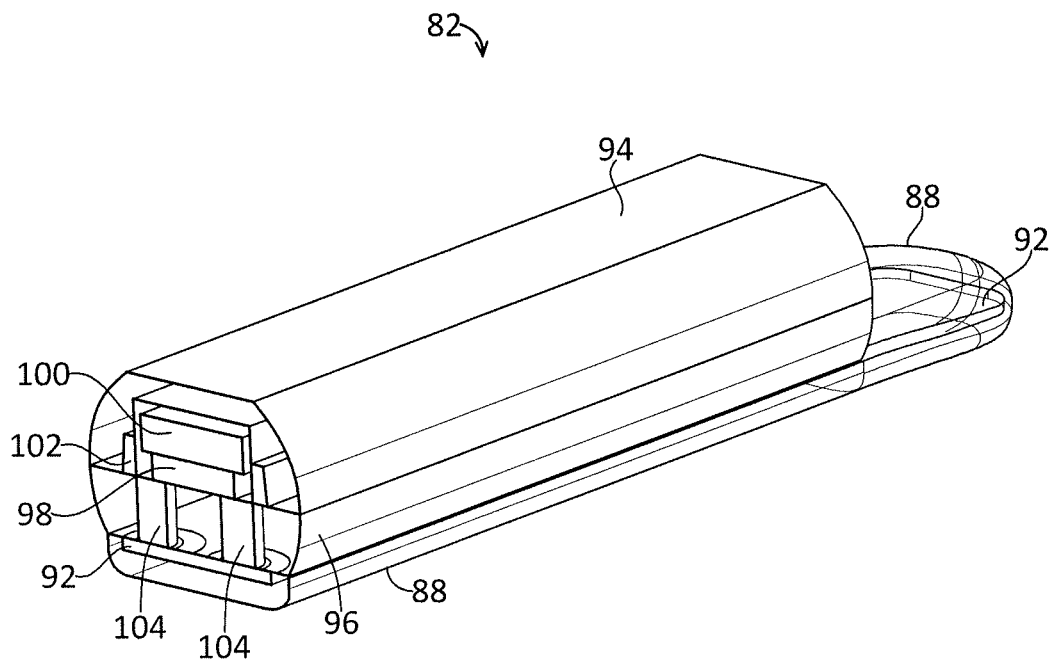
FIGS. 5A and 5B illustrate perspective sectional and front sectional views, respectively, of an exemplary first portion of an implant.
Figure 5B:
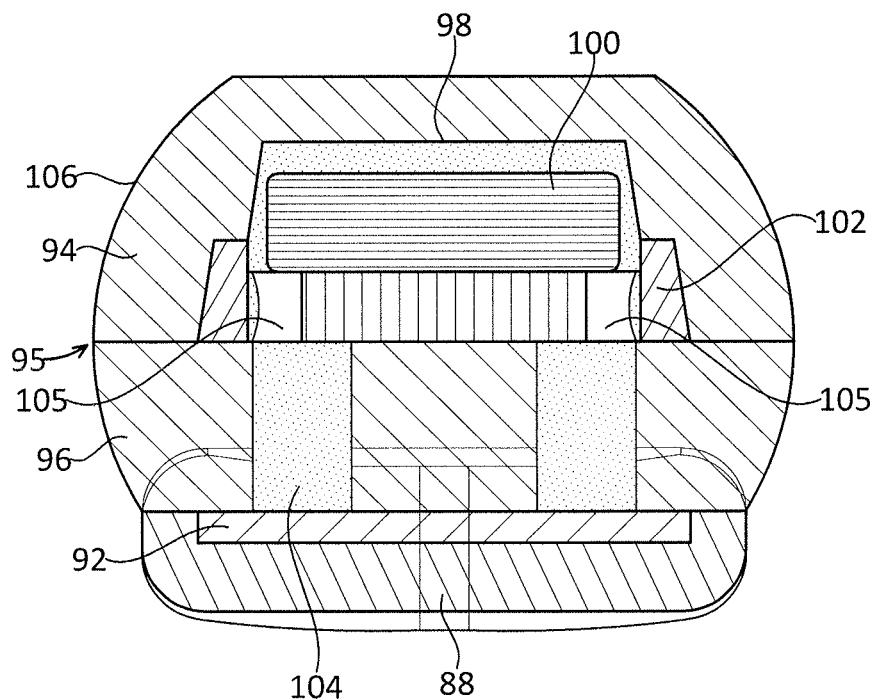

FIGS. 5A and 5B illustrate perspective sectional and front sectional views, respectively, of first portion 82. First portion 82 includes top and bottom housings 94 and 96, respectively, that interface at hermetic seal 95. The flexible electronics on substrate 92 are in electrical communication with vias 104, which are electrically coupled to housing electronics such as processor 98 (which can be an ASIC) and rechargeable battery 100. Optional water getter 102 is also disposed in the top portion of first portion 82.

First portion 82 also includes coating 106 thereon, which can be, for example without limitation, gold.

Figure 6A:
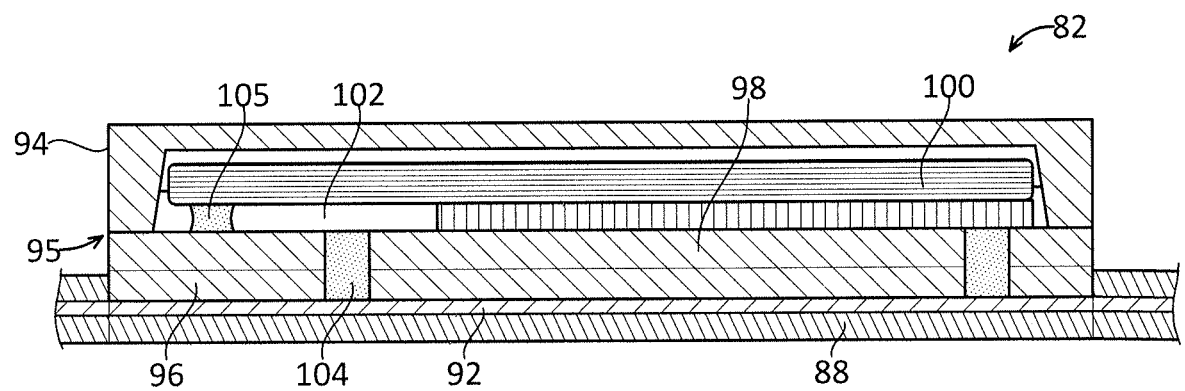
FIGS. 6A and 6B show side assembled and side exploded view of the exemplary first portion of an implanted device from FIGS. 5A and 5B.
Figure 6B:
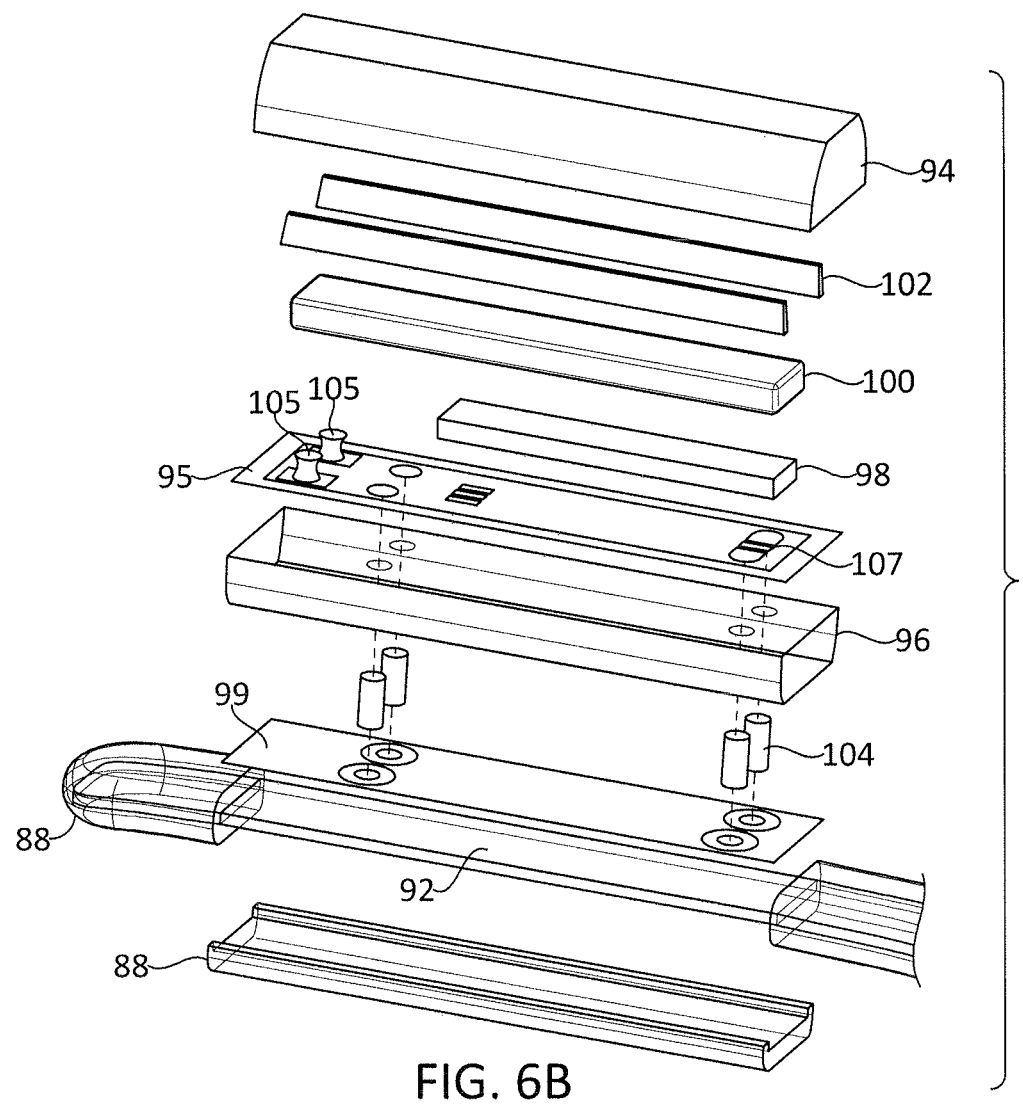

FIGS. 6A and 6B show side assembled and side exploded view of first portion 82 of an implanted device from FIGS. 5A and 5B. This first portion can be incorporated into any of the other embodiments herein. The relevant description of FIGS. 5A and 5B can similarly apply to FIGS. 6A and 6B. FIG. 6B illustrates more clearly the assembly and the manner in which the components are electrically coupled. The housing includes metallization 99, which provides an electrical connection with the flexible electronics on the substrate 92. Disposed between top housing 94 and bottom housing 96 is seal 95 and electrical connections 107, which are electrically coupled to vias 104. Connects 105 are in electrical communication with battery 100.

Figure 7A:
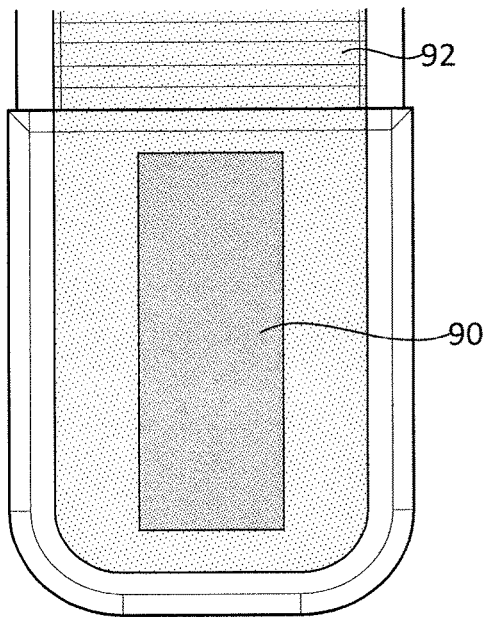
FIGS. 7A, 7B and 7C illustrate an exemplary sensor portion of an implant.
Figure 7B:
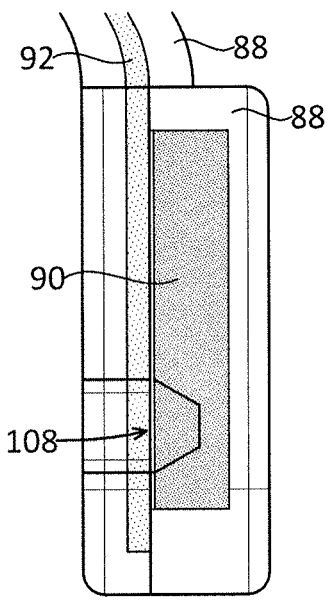
Figure 7C:
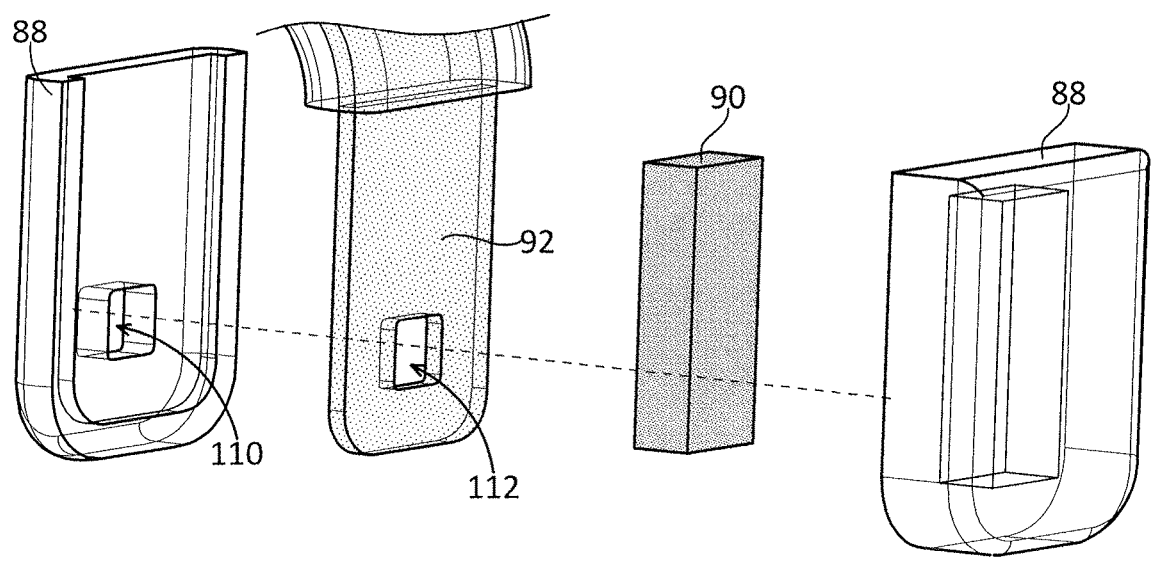

FIGS. 7A, 7B and 7C illustrate exemplary sensor portion 84 from FIGS. 4A-4C, but can be any of the sensor portions herein. FIG. 7A is a front view, FIG. 7B is a side view, and FIG. 7C is an exploded perspective front view. What can be seen is that encapsulation 88 and substrate 92 both include aligned windows or apertures therein, which allows the pressure sensor to communicate with the external environment. The windows together create opening 108 (see FIG. 12B) in the sensor portion. The windows may be filled with a material that allows pressure to be communicated to pressure sensor. The pressure sensor is "face down" on the flexible substrate and thus able to sense pressure via the access holes shown. The sensor electrical contact pads can be directly in contact with electronics on the flexible substrate, which can remove the need for wiring/wire bonding and requires an opening in the flex substrate and an opening in the encapsulation. Conductive lines/bond pads, and optional Parylene C coatings at piezo bridges are not shown in the figures, but can be included.

In any of the delivery procedures herein, an incision made in the eye during delivery can be 1 mm oval, or may be 1.2 mm.

FIGS. 8A-8E illustrate an exemplary embodiment of implant 140 and exemplary delivery device. In this exemplary embodiment, the implant does not include a flexible elongate connector portion with a bend as in some of the embodiments above.

FIG. 8A shows a portion of implant 140. Sensor 142 is disposed at a first end of implant 140, and is coupled to housing 144. Housing 144 can include any components of any of the first portions herein. Housing 144 includes the encapsulation that encapsulates antenna 152, controller 150 (e.g., an ASIC), power source 146, and feedthrough 148 that connects ASIC 150 to the antenna 152. As in other embodiments herein, implant 140 can also include a metallic coating on the glass housing for hermeticity, one or more electrical lines on one or more glass or titanium substrates, an antenna ground plane, and a water getter (inside housing).

FIGS. 8Bi and 8Bii illustrate implant 140 from FIG. 4A but includes a biocompatible cover 160, optionally a polymeric material, including a plurality of sensor protective flaps 162 that extend at a first end (two are shown), a mechanical stop 164 for interfacing with a delivery device for insertion, and a conical second end 166 to ease the injection. Implant 140 is disposed inside cover 160, with two sides of sensor 140 protected by the flaps 162. Top and bottom sides of sensor 142 are not covered by cover 160.

Figure 8C:
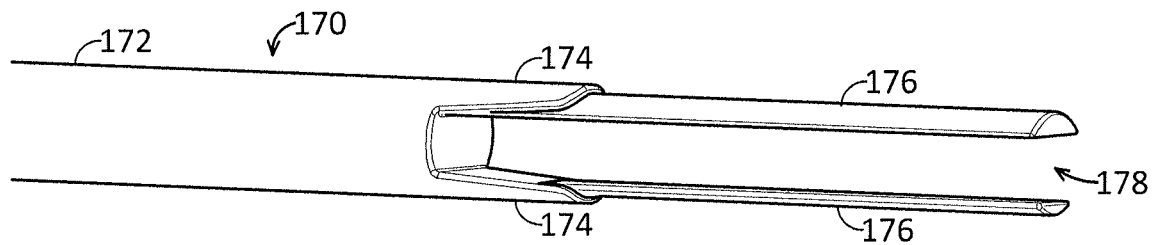
FIGS. 8A, 8Bi, 8Bii, 8C, 8D and 8E illustrate an exemplary embodiment of an implant and an exemplary delivery device.
Figure 8D:
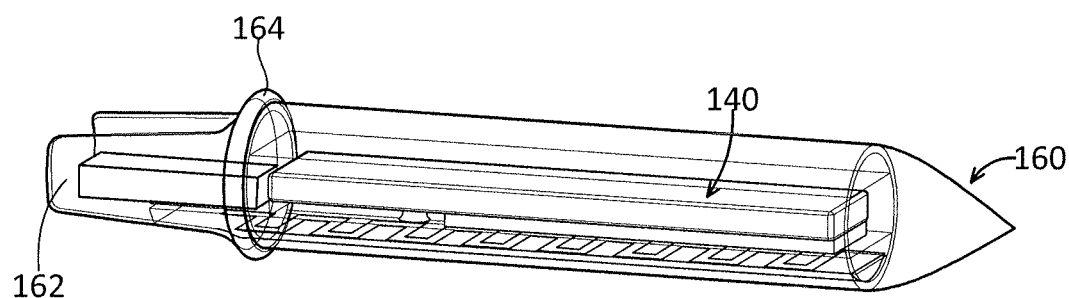
Figure 8E:
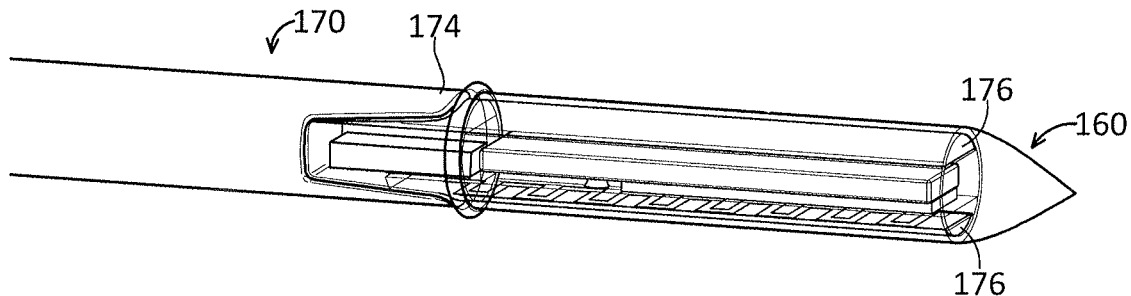

FIGS. 8C and 8E illustrates an exemplary delivery tool 170 adapted and configured to interface with cover 160 (with implant 140 therein), which is shown in FIG. 8D, but inverted relative to FIG. 8Bi. Delivery tool 170 is adapted to facilitate the implantation of implant 140 and cover 160. Delivery tool 170 includes a main body 172 from which extend a first plurality of extensions 174 and a second plurality of extensions 176 (in this embodiment there are two of each). Extensions 174 are shorter than extensions 176 and are radially outward relative to extensions 176. One of the extensions 174 is aligned with one of the extensions 176, and the other of extensions 174 is aligned with the other of extensions 176. The plurality of extensions 174 interface with stops 164 of cover 160 when cover 160 is fully advanced within the inner space 178 of tool 170. Arms or extensions 162 on cover 160 are similarly sized and configured to fit within the space defined by arms 174. The radially inner arms 176 are positioned just slightly radially inward, and are sized and configured to be disposed within elongate channels within cover 160, which can be seen in FIG. 8E. In this embodiment body portion 172 of tool 170 has the same or substantially the same outer diameter as the cover 160. The elongate arms 176 can stabilize the relative positions of tool 170 and the implant during the delivery process.

Figure 9A:
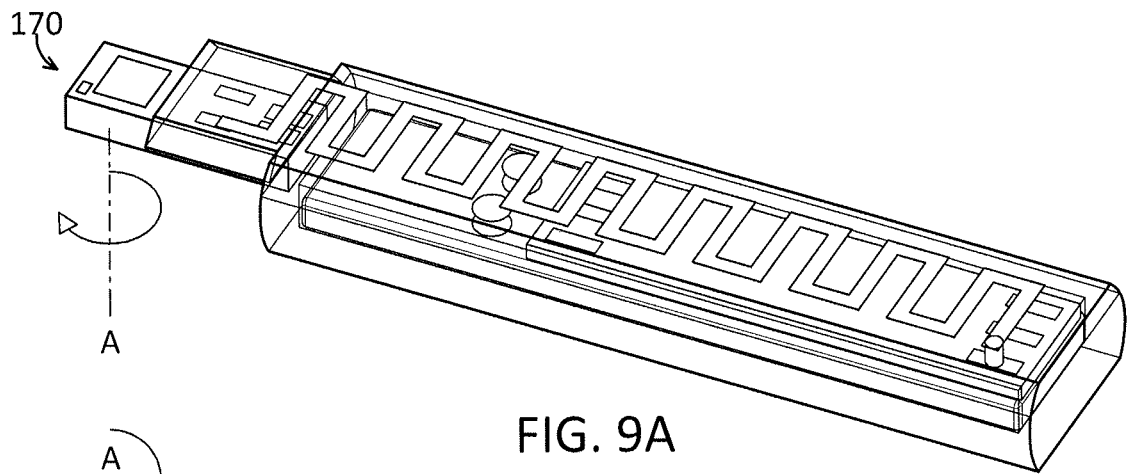
FIGS. 9A, 9B and 9C illustrate an exemplary implant, wherein the implant is adapted such that the sensor can rotate relative to the main housing about an axis, and the rotation axis is perpendicular relative to the main implant body.
Figure 9B:
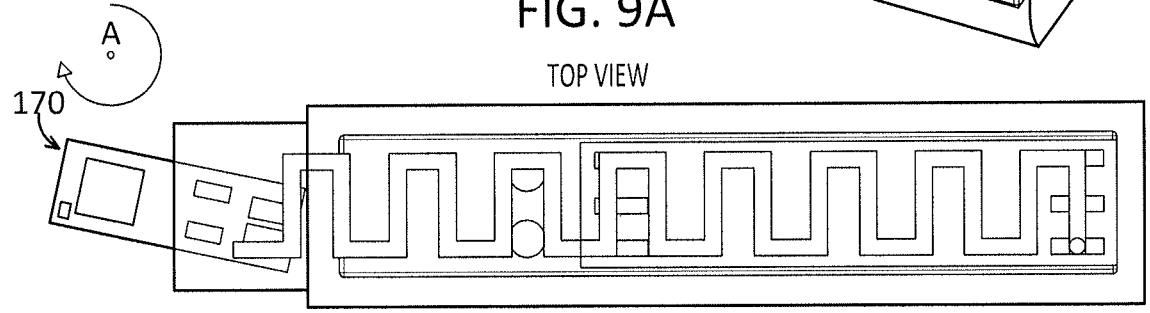
Figure 9C:
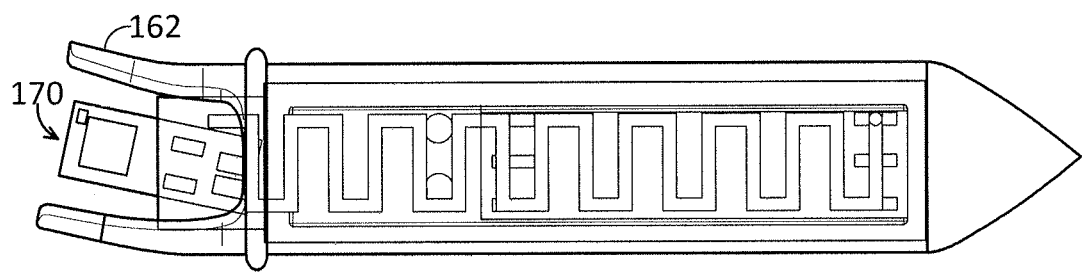

FIGS. 9A-9C illustrate an exemplary alternative embodiment to that shown in FIGS. 8A and 8B, but in this embodiment the implant is adapted such that sensor 170 can rotate relative to the main housing about axis "A," and the rotation axis is perpendicular relative to the main implant body. All other components are described above and are not relabeled for clarity. FIG. 9A is a perspective view, and FIG. 9B is a top view. FIG. 9C is a top with cover, showing the two arms flexing with the rotation of the sensor. The protective cover follows the sensor orientation, as shown in FIG. 9C. In some embodiments the sensor can rotate up to 90 degrees, and in some embodiments no more than 45 degrees, such as 40 degrees or less, or 35 degrees or less, or 30 degrees or less, or 25 degrees or less, or 20 degrees or less, such as 12 degrees. In some embodiments the sensor is rotatable from 0 to about 90 degrees (e.g., 95 degrees). The implant in FIGS. 9A-C can be the same as the implant in FIGS. 8A-E in all other regards.

Figure 9D:
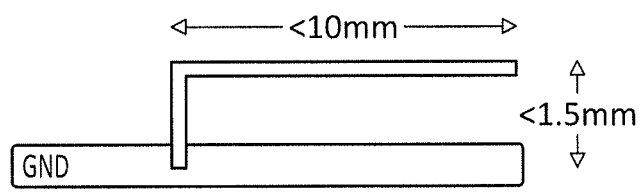
FIGS. 9D and 9E illustrate merely exemplary antenna design and placement in any of the implants herein.
Figure 9E:
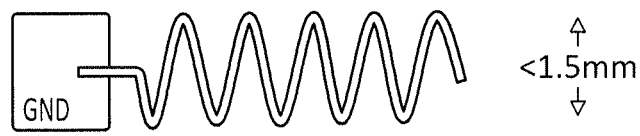

FIGS. 9D and 9E illustrate merely exemplary antenna design and placement in any of the implants herein. The antennas in the implant in FIG. 9A-9C can have other configurations and sizes as well.

Exemplary lengths for the implants shown in FIGS. 8A and 8A (without the cover) are 3-5 mm, such as 3.3 mm to 4.7 mm, such as 3.5 mm to 4.5 mm, such as 3.7 mm to 4.3 mm, such as 4 mm. Exemplary lengths for the covers herein, such as cover 160 from FIG. 8Bi are 4 mm to 6 mm, such as 4.3 mm to 5.7 mm, such as 4.5 mm to 5.5 mm, such as 4.7 mm to 5.3 mm, such as 5 mm. Exemplary widths for the implants shown in FIGS. 8A and 8A (without the cover) are 0.5 mm to 1.5 mm, such as 0.7 mm to 1.3 mm, such as 1 mm.

Figure 10A:
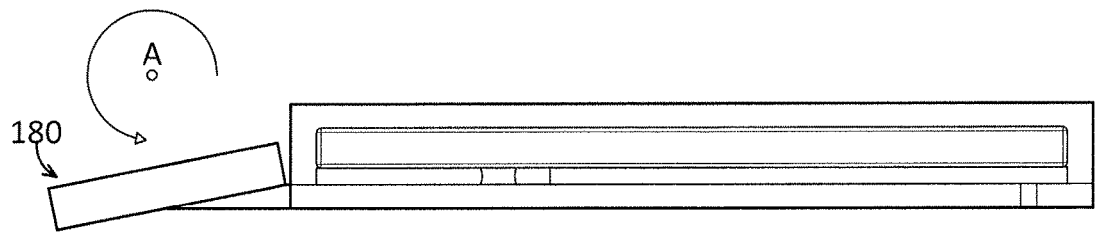
FIGS. 10A and 10B (side and top views, respectively) illustrate an exemplary implant that is adapted such that the sensor can rotate relative to the main housing about an axis, such that is can flex up or down relative to the elongate axis of the main housing.
Figure 10B:
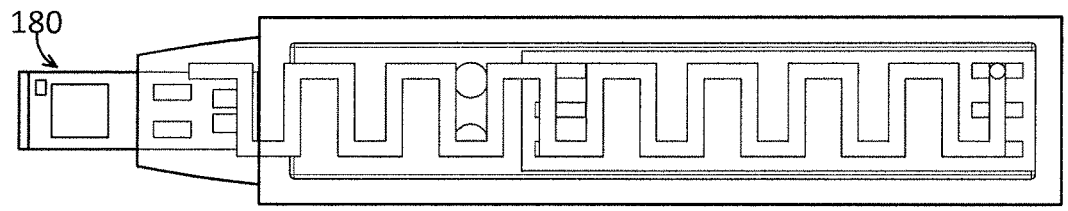

FIGS. 10A and 10B (side and top views, respectively) illustrate an alternative implant similar to that shown in FIGS. 9A-C, but in this embodiment the implant is adapted such that sensor 180 can rotate relative to the main housing about axis "A," such that is can flex up or down relative to the elongate axis of the main housing. This embodiment may benefit from an angled sensor contact plane in the substrate.

Figure 11A:
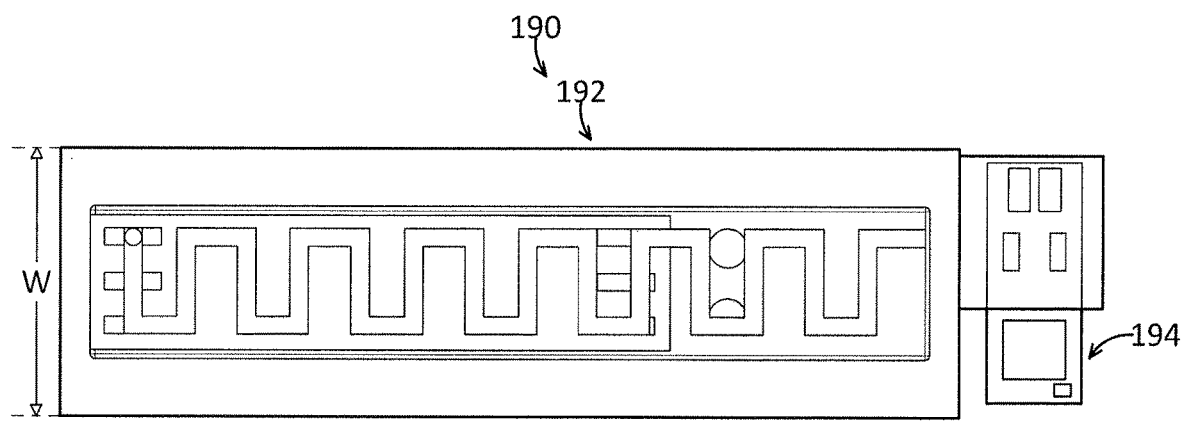
FIGS. 11A and 11B (top and side views, respectively) illustrate an exemplary implant that includes a main body and a sensor.
Figure 11B:
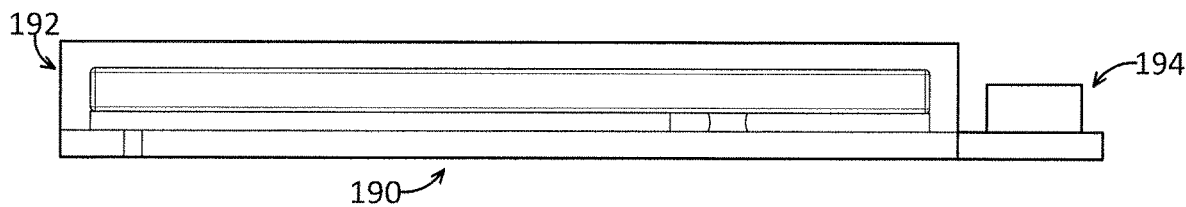

FIGS. 11A and 11B (top and side views, respectively) illustrate an alternative implant 190, which includes main body 192 and sensor 194. Main body 192 can include any of the components set forth herein. Width W of the body 192 is wider than in FIGS. 9 and 10, and sensor 194 is oriented degrees relative to the sensor in the embodiment in FIG. 9A. Implant 190 can also be adapted such that sensor 194 can rotate with respect to main body 192. In some exemplary embodiments the sensor has a width that is about 0.3 mm to about 2 mm, such as from 0.5 mm to about 1.5 mm.

FIGS. 12A-12F illustrate an exemplary implant 200 that has more of a square configuration that embodiments above. At least a portion of the implant has more of a square configuration, even if there are one or more arms extending from a main body portion.

Implant 200 includes an outer cover 210 and internal portion 220. Any of the description herein relative to covers can also apply to cover 210, and any of the components described above can also be included in internal portion 220 (e.g., battery, processor, antenna, etc.). For example, internal portion 220 can include any or all of the components found in internal portion 140 shown in FIG. 8A, but they are organized within the implant in a different manner.

Figure 12A:
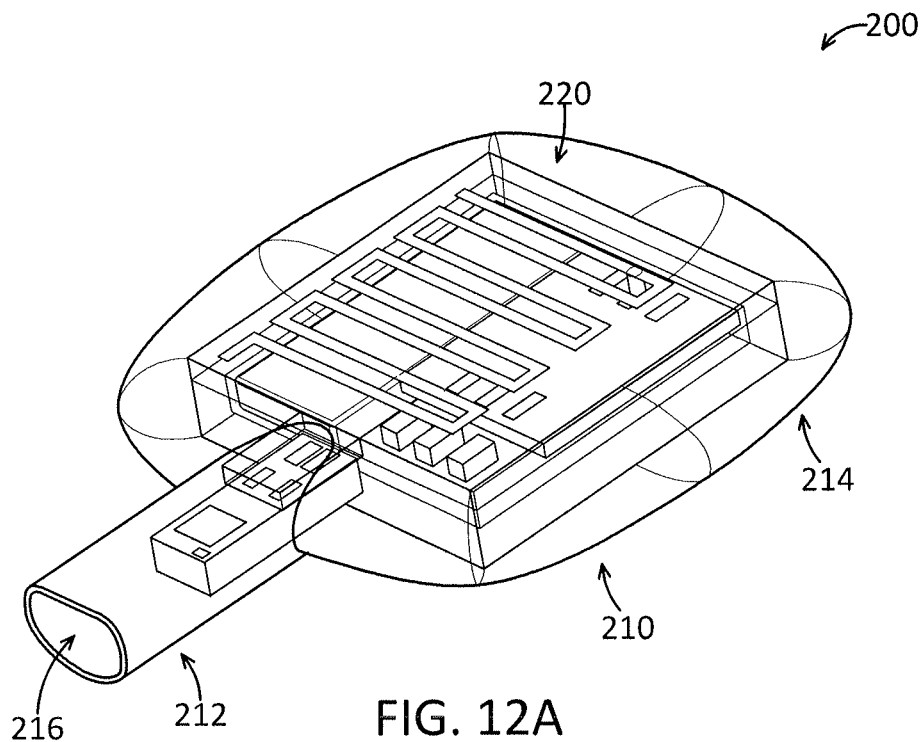
Figure 12B:
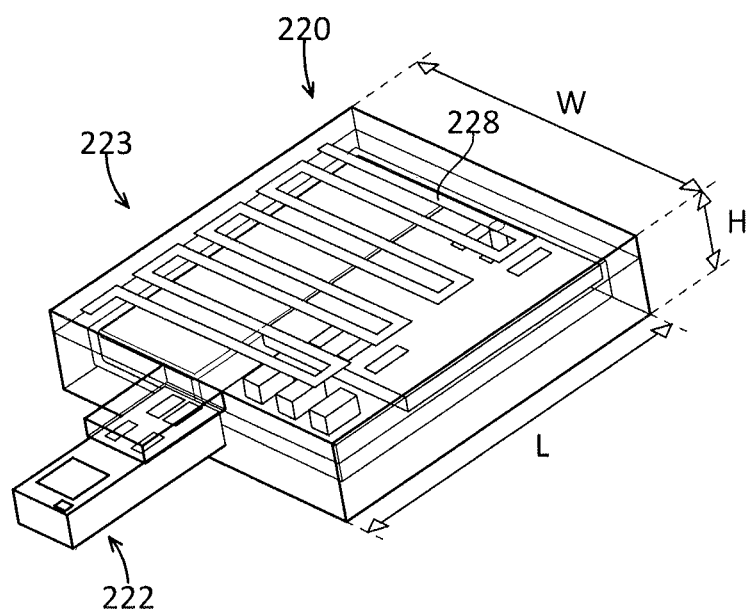

Figure is a bottom perspective view with the cover 210 on internal portion 220. FIG. 12B is the same view from FIG. 12A without cover 210. FIG. 12C is a front view of internal portion 220 without cover 210. FIG. 12D is a bottom view without cover 210. FIG. 12E is a top view without cover 210. FIG. 12F is a top view including cover 210. FIG. 12G is a front view including cover 210.

Internal portion 220 includes a main body portion 223 from which sensor 222 extends. The square configuration can make it easier to implant the implant in certain places in the eye. Main body portion 223 has a square configuration, with Length L and width W being the same dimensions. Body portion 223 can have, however, slightly rectangular configurations as well. Cover 210 similarly has a main body portion 214 with a generally square configuration and an arm portion 212 extending therefrom. Arm 212 has an open end defining lumen 216 so pressure sensor 222 can communicate with the environment.

Internal portion includes bottom housing 221 and top housing 225 (see FIG. 12C) that interface at a hermetic seal, examples of which are described herein. The internal portion also includes antenna 228 disposed in the bottom portion of the internal portion 220, battery 224, pressure sensor 222, processor 226 (e.g. ASIC), and electrical connect or via 227.

Other aspects of any of the embodiments herein can similarly apply to implant 200.

It is essential to provide a hermetic seal around the whole implant in order to ensure long term biocompatibility and also eliminate the risk of ocular fluids coming in contact with the miniature electronic circuit boards comprising the implant, potentially causing short circuits and other failures, including corrosion. In some embodiments, a hermetic seal may be formed by encasing the whole implant in a non-permeable material such as glass or Titanium, then closing the casing by means of laser welding, anodic bonding, or other types of sealing process that causes localized heating and fusion but does not cause a significant rise in temperature of the contents of the implant, for example, less than 2 degrees C. A challenge arises when designing a hermetic seal for a pressure sensor module, since it is necessary for the anterior humor of the eye to transmit its pressure to the sensor element inside the hermetically sealed implant in order to obtain reliable measurements of IOP.

Figure 13:
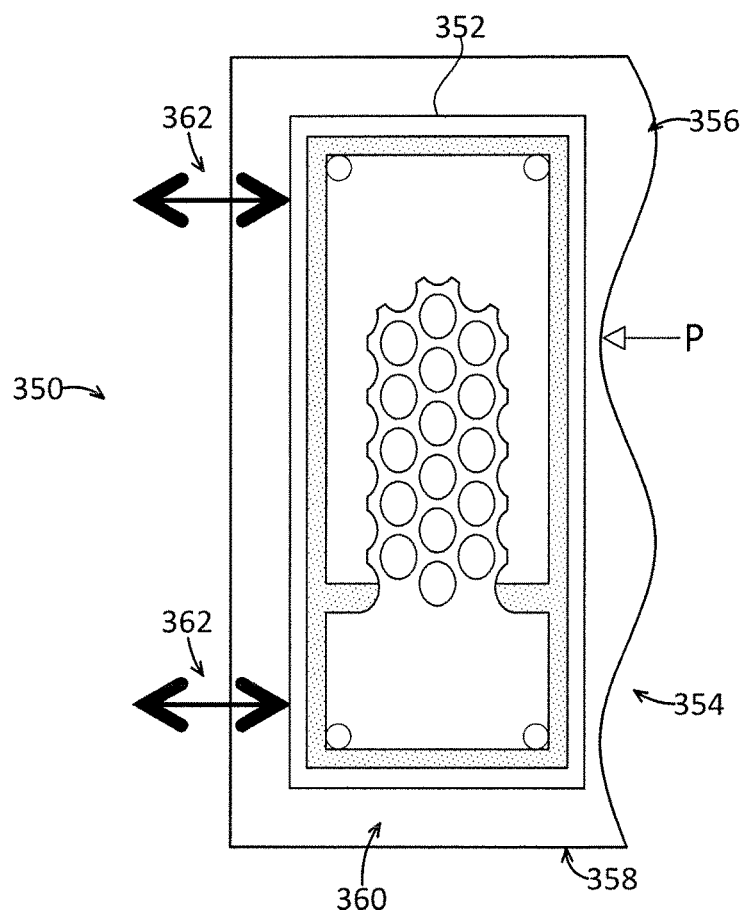
FIG. 13 illustrates a portion of an exemplary implant in which a pressure sensor is hermetically sealed inside a fluid chamber.

FIG. 13 illustrates a portion of an exemplary implant 350 in which pressure sensor 352 is hermetically sealed inside chamber 354. This concept of a fluid-filled chamber in which a pressure sensor is disposed can be incorporated into any implantable device herein. Chamber 354 includes a casing 358 and thin flexible membrane 356, which together define an outer wall of the implant. The implant also includes vias 362 that electrically connect pressure sensor 352 to other implant electronics, as described elsewhere herein. The chamber also includes inert fluid 360 contained within the chamber 354. Thin flexible membrane 356 is thin and flexible enough that it will transmit pressure P exerted by the anterior humor to fluid 360 within the chamber, which transmits the pressure to pressure sensor 352. In some embodiments flexible membrane 356 can be between 2 microns and 50 microns, such as 2-25 microns, such as such as 2-20 microns, such as 2-15, such as 2-10 microns, such as 5-10 microns. In some embodiments flexible membrane can be made of titanium or parylene. In some embodiments casing 358 can be made of titanium (e.g., TiN) or glass, and optionally coated with ceramic, examples of which are described herein. Examples of fluid 360 include, without limitation, nitrogen and silicone oil. The remainder of implant 350 can be the same as any of the other implants described herein.

In some embodiments the sensor comprises a piezoelectric sensing element where an inert fluid in the fluid chamber transmits hydrostatic pressure to the sensing element through the flexible membrane. In some embodiments the sensor comprises a capacitative sensing element wherein an inert fluid in the fluid chamber transmits hydrostatic pressure to the sensing element through the flexible membrane.

Any of the implants herein can have an unfolded length between about 2 mm to about 20 mm, such as between 2 mm and 15 mm, such as between 3 mm and 10 mm, such as about 7 mm. The housing can have a length of between 1 mm and 8 mm, such as between 1 mm and 7 mm, such as between 1 mm and 6 mm, such as between 2 mm and 5 mm, such as about 3 mm, or 3.3 mm.

The implants herein should be easy to surgically implant, and can optionally be implanted using a scleral tunnel or a clear corneal incision of perimeter less than 3.0 mm, optionally using a punch incision with a needle of outer perimeter preferably less than 1.2 mm, more preferably less than 1.0 mm. The implant should have long term biocompatibility, should not cause tissue erosion, should not cause the loss of corneal endothelium, and should not touch the iris, which will lead to deposition of iris pigment. The implants should provide a routine explantation option. The implants are preferably implanted in the sclera, or the conjunctiva, with the sensor being placed in the anterior chamber, posterior chamber, or inside the lens capsule as in the form of a capsular ring, while it may also be attached to an intraocular lens, the iris, the ciliary bodies, or be sutured to the ciliary sulcus.

In some embodiments the overall implant dimensions are less than 4.0 mm×1.5 mm×1.0 mm, preferably less than 3.5 mm×1.5 mm×1.0 mm, more preferably less than 2.5 mm×2.5 mm×1.0 mm, and most preferably less than 2.5 mm×2.5 mm×0.500 mm.

Any of the implants herein can have a folded length (after a portion of the implant is folded, or bent) between about 1 mm and 15 mm, such as between 1 mm and 12 mm, such as between 2 mm and 10 mm, such as between 3 mm and 9 mm, such as between 4 mm and 8 mm, such as between 5 mm and 7 mm, such as about 6 mm.

Exemplary pressure sensor dimensions can be 0.5 mm-1.5 mm×0.5 mm-2 mm. Off-the-shelf pressures sensors may be used in some embodiments.

Any of the implant housings herein, such as bottom housing 221 and top housing 225 in FIG. 12C (which may also be referred to as "casing" herein) can in some embodiments comprise glass or titanium with a gold or titanium plating (or any other biocompatible metal coating). The flexible connector, in embodiments that include one, can be a variety of suitable materials, such as, without limitation, a polymeric material encapsulated in a biocompatible silicone elastomer. The pressure sensor portion of any of the implants can include a sensor flexible membrane (e.g., Glass/Silicon), with other sides encapsulated in a silicone elastomer. In some embodiments the implant can have a parylene C coating on sensor membrane edges.

In any of the embodiments, any of the housings, such as a top housing or a bottom housing, can have a wall thickness of about 25-200 microns, such as about 50-150 microns, or about 75-125 microns, or about 100 microns. The wall thickness can provide hermeticity over a 10 year lifetime. Any of coatings herein can be about 0.1 micron to about 10 micron, such as about 0.1 micron to about 5 micron. The housings can comprise bonded top and bottom portions interfacing at a seal, as shown. The housings can have any of the following exemplary general shapes or configurations to provide a delivery profile that enables 1.0 mm external diameter: square, oval, circular, C-shaped, rectangular, chamfered, etc. The housings in FIGS. 5A and 5B, for example, have outer surfaces that are C-shaped, which allows the device to have a smaller profile than it would have with, for example, a more rectangular configuration.

Figure 14A:
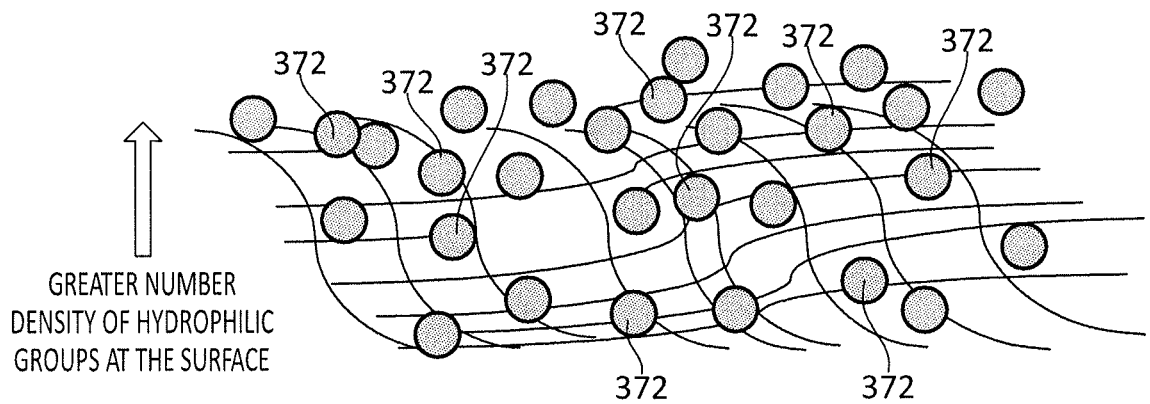
FIGS. 14A and 14B illustrate that some exemplary implants can be coated with a biocompatible coating that may be optionally infused with weakly bonded to an anti-inflammatory agent or an anticoagulant.
Figure 14B:
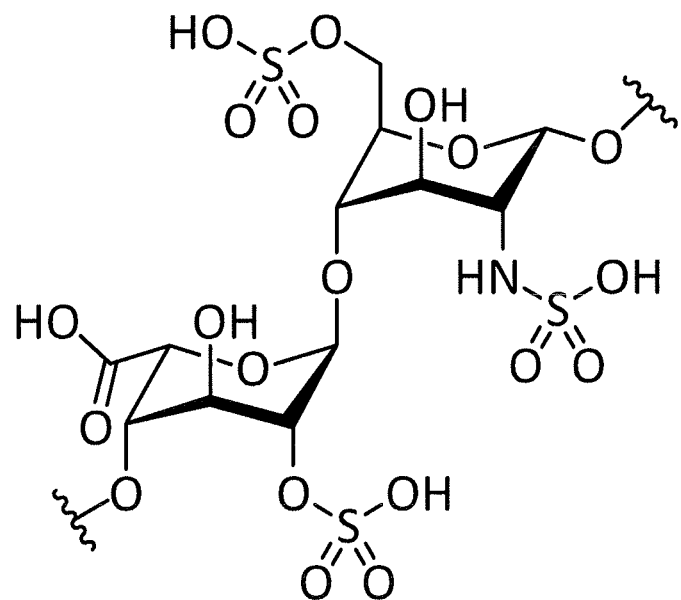

In some embodiments the implant is coated with a biocompatible coating that may be optionally infused with weakly bonded to an anti-inflammatory agent or an anticoagulant, which is illustrated in FIGS. 14A and 14B. The coating can be comprised of a cross-linked amphiphilic polymer with hydrophobic and hydrophilic segments. Typical polymers include hydrogels, silicone hydrogels and the like, with equilibrium water content ranging from 30% to 90% by weight. The cross-linked polymer comprising the coating folds such that the number density of hydrophilic groups increase towards the outer surface of the coating, while the surface contacting the implant may be richer in hydrophobic groups. This coating may include hydroxyl groups, amino groups, amides, sulfhydryl groups, thiols, as well as ionic moieties such as ammonium groups, alkyl ammonium groups and the like. These groups on the cross linked network comprising the coating are used to hydrogen bond or electrostatically bond anticoagulants such as Heparin sulfonate. FIG. 14A shows anti-inflammatory agents or anticoagulant groups 372, with the remainder of the groups being hydrophilic groups. An example of an anticoagulant is heparin, which is 13-20 kDa.

The hydrogel layer can have a gradient in number density of hydroxyl groups, wherein the gradient is in the opposite direction of the gradient in cross-link density.

The outer surface of the coating may be patterned or textured in order to promote fixation into the muscle in which the implant is positioned. The design of the texture is optimized to cause a minimal level of fibrosis causing adhesion of tissue to the implant without unduly enhancing immune response to the implant or chronic inflammation. Table 1 includes examples of components that may be included in such coatings.

TABLE 1

| Hydrophilic Monomers | Hydrophobic Monomers | Cross-Linking Agents | Anticoagulants |
|---|---|---|---|
| Hydroxyethyl methacrylate | Methyl methacrylate | Ethylene Glycol dimethacrylate | Heparin |
| Glyceryl monomethacrylate | Styrene | Bis Acrylamide | Antithrombin |
| Acrylic acid | Furfuryl acrylate | | Direct thrombin inhibitors lepirudin, desirudin, bivalirudin, argatroban. |
| Methacrylic acid | | | |
| Trimethylol propane triacrylate | | | |

Any of the power sources herein can be a battery or capacitor, such as a solid-state thin film battery, with an internal electrical connection to the controller, which can be an ASIC.

Any of the implants herein can have any of the following electronics: a controller such as an ASIC, electrical connections to sensor (such as flexible electronics on a substrate), hermetic via in a housing bottom portion, electrical connections to an antenna (such as flexible electronics on a substrate, and internal connections to the battery, and discrete electronic components (resistance, capacitance and/or inductance). In some embodiments that include an ASIC, the ASIC is ultra-low power to reduce the size of the overall implant.

In any of the embodiments herein, the ASIC can include a microelectronic circuit comprising a microcontroller, a flash memory, a non-volatile memory and a logic circuit. The logic circuit can include power management and data management modules. The ASIC can include a microelectronic circuit wherein said microelectronic circuit comprises conductive connectors of width in the range 36-360 nanometers.

Any of the implants herein can also include a $H_2O$ getter, adapted to absorb moisture migrating through the housing to extend device lifetime with humidity below target 5000 ppm.

In some embodiments one or more components of the implant can be configured to correspond, or match, the curvature of one or more anatomical locations within the eye. This can lead to better compatibility within the eye.

The functionality of one or more components in the device can influence the overall size of the implant. For example, more battery power generally requires a larger battery size, which increases the size of the implant. Similarly, the size of an internal memory can increase as more memory is needed to store sensed data (e.g., temporarily). One or more ASICs can be used to manage the onboard components. It may be generally desirable to make the implant components as small as possible, but without sacrificing desired functionality. Determining how much sensed data is desired and/or the frequency of data sensing can thus influence the overall size of the implant.

In any of the embodiments herein, the antenna can have a space filling design, meaning that a maximum length of antenna is provided within a specific area, and wherein the antenna is connected to an electrical circuit that can be adjusted for its electrical impedance as a function of its resistive load. Examples of space filling antenna designs can be found in, for example, U.S. Pat. Nos. 7,148,850 and 7,026,997, the disclosures of which are incorporated by reference herein.

In any of the suitable embodiments herein, the antenna is disposed on a ceramic substrate disposed inside a housing, wherein the antenna has a thickness in the range of 100-500 microns.

In any of the embodiments herein, the circuit comprising the antenna can have a Q factor in the range of 10-50 under use conditions.

In any of the embodiments herein, the antenna includes vacuum deposited metal filaments on a ceramic substrate.

In any of the embodiments herein, the antenna has a conductive length of not less than 15 mm and not more than 100 mm.

In any of the embodiments herein, the antenna is adapted so that it transmits electromagnetic energy at a frequency that is not harmful to the human body.

Any of the implants herein can have more than one pressure sensor therein, or secured thereto.

Figure 15:
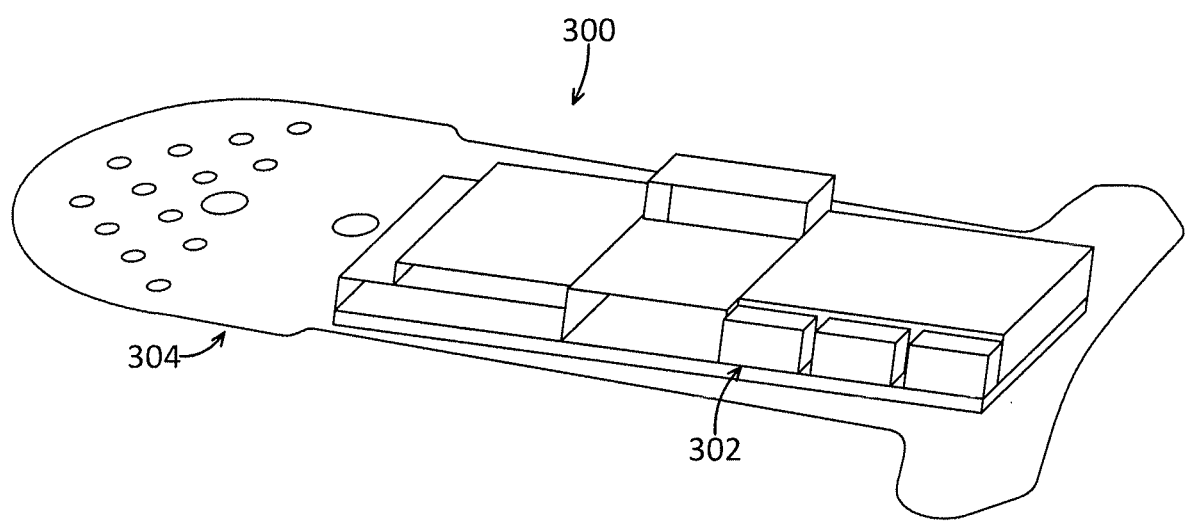
FIG. 15 illustrates an exemplary implant that includes sensor and electronics mounted on an exemplary glaucoma draining device.

FIG. 15 illustrates an exemplary implant 300 that includes sensor and electronic 302 mounted on a glaucoma draining device 304, such as those manufactured by SOLX™. FIG. 15 illustrates a device that can both monitor pressure (using any of the electronic components and configurations herein in portion 303) and treat high IOP. Additional sensors can be implemented to detect oxygenation and proteins.

Figure 16:
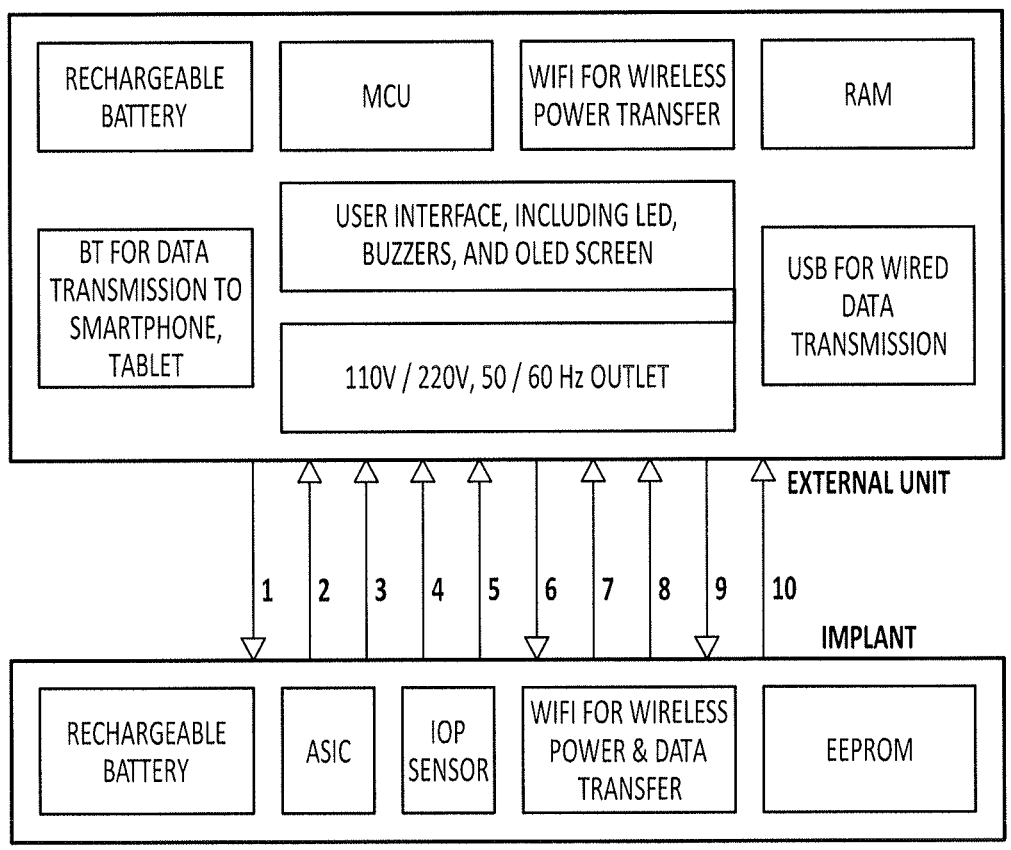
FIG. 16 illustrates an exemplary implant and an exemplary external device, and an exemplary communication protocol between the implant and external device.

In any of the embodiments herein, the implant is adapted to sense IOP of an eye, or a portion of the eye. Any of the implants herein can include erasable memory. In some embodiments the system includes one or more external interrogation devices ("EID"s) that are disposed outside of the eye and can be adapted to communicate (preferably wirelessly) directly or indirectly with the implant. The EID is used to recharge the battery disposed in the implant, receive intraocular pressure data from the implant and reprogram the firmware embedded in the ASIC of the implant, when required. Communication between the implant and the EID follows a protocol, and example of which is shown in FIG. 16. This protocol involves encrypted data exchange, said encryption being compliant with all applicable Governmental regulations controlling confidentiality of medical information. Such a communication protocol also includes a handshake between the EID and the implant, the EID being the Master and implant being the Slave in this protocol. The exemplary protocol in FIG. 16 includes the following steps: 1) I am ready to transmit power and receive data; 2) I am ready to receive power, receive data, and I have data to transmit; 3) Transmission of data for initialization (code, time stamp, resonance frequency); 4) Data transmission (always recharging first step, when completed, data transmission (second step), when completed data transmission from External Unit to Implant (third step)); 5) Data transmission complete; recharging can begin in 2 seconds; 6) Wireless power transmission; 7) Threshold voltage reached, stop power transmission; 8) I am ready to receive data transmission (data for LUTs; reprogramming of firmware); 9) I have data/no data to transmit; 10) Data transmission, if step 9 gives code for data to transmit.

The one or more EIDs can receive information from the implant, such as pressure data (raw or processed) or other data indicative of pressure. The EIDs can also transmit information to the implant, such as instructions for programming or reprogramming some operational functionality of the implant (sensing software in the implant). One or more EIDs can also communicate with other EIDs, or external databases. An EID can also transfer power to the implant.

In some embodiments the system includes a patient EID (e.g., smartphone or a dedicated electronic device or an add-on device to a smartphone), which can be used or controlled by the patient. A patient EID can be used to charge the implant, receive data from the implant (e.g., by querying the implant), and optionally reprogram one or more algorithms stored in the implant. A patient EID can be wearable (e.g., wristband, watch, necklace) or non-wearable (e.g., smartphone, smartphone add-on, bedside device).

Systems herein can also include one or more physician EIDs, which can be wearable or non-wearable (e.g., dedicated electronic device, or laptop, smartphone or tablet add-on). For example, a physician can have access to one handheld EID (e.g., smartphone or tablet add-on), and have access to another medical personnel EID (e.g., a laptop computer with additional hardware and software capabilities). Any of the EIDs herein can be adapted to perform any of the EID functions described herein.

System software, on one or more of the EIDs, can be adapted to download and/or upload sensed pressure data, or information indicative or sensed pressure data to one or more EIDs or to the implant. System software includes software for data storage, data processing, and data transfer. System software can also facilitate communication between the patient EID and one or more physician EID (or other remote device).

The systems herein can also include one or more software and/or firmware applications to collect, compile, and/or store individual sensor data (e.g., sensor measurements) for diagnostic or treatment evaluation support by the medical personnel (e.g., ophthalmologist). The software and/or firmware may exist on one or more EIDs, or in some instances may be disposed on or more implantable devices. The systems herein can also include one or more software applications to collect and/or compile multiple sensors data as a basis for medical data analysis, allowing support for, e.g., predictive medicine.

Management of data can include processing of raw signals to, e.g., filter noise and enhance signal to noise ratio, application of algorithms that recognize and select a true pressure data from spurious signals, further processing of data to, e.g., recognize and document 1 hour to 30 day trends in pressure, and reprogramming of the ASIC and device firmware in response to specific data trends or command by caregiver.

Theoretically, a truly continuous monitoring of IOP requires continuous monitoring of IOP at a frequency exceeding the most rapid spike in IOP recorded (approx. 30 Hz). In reality, the data generated by such a sensor will be of such a magnitude that it will be difficult to manage even with frequent downloading of data, and will also require a large battery in order to manage the daily power consumption of such a device. In some embodiments an optimum amount of pressure data is therefore collected per day, based on patient needs, needs of treatment, upper limit of power available, and size of the memory units in the device.

In some embodiments the resolution and accuracy of IOP data range from 0.2 mmHg to 1.0 mmHg and form 0.5 mmHg to 2 mmHg, respectively. In some embodiments the frequency of data acquisition is minimum 2/day to maximum 1/15 min. In some embodiments the frequency of recharge is less frequently than 1/day. In some embodiments the frequency of data transmission to a caregiver can be once a day or more. In some embodiments wireless recharging and data exchange is performed using inductive coupling or electro-magnetic coupling among magnetic and/or electric antennas respectively, uses a body safe frequency and intensity, and with minimum attenuation by human tissue. The implants should have a 10 years life of battery, and have hermetically sealed package.

The sensed data and/or data indicative of the sensed data can be stored in one or more proprietary databases. In some embodiments all of the database information must be reviewed by a physician before being included in the database. In these embodiments the patients do not have access to the database. One or more databases can store time histories of sensed pressure measurements, or time histories of data indicative of sensed pressure.

The one more databases can include lookup tables with threshold pressures values, such that future sensed pressure data can be compared to the data in the lookup tables. The lookup tables can be for an individual or across a population of individuals. The lookup tables can be updated with new pressure data from one or more implants and one or more individuals. In some embodiments threshold levels can be a factor relative to therapy, optionally automatic drug delivery or a drug regimen. In some embodiments the sensed data can be used in a closed loop treatment loop. For example, pressure sensed over time can be input to a closed loop patient therapy protocol, such as closed loop drug therapy protocol.

Figure 17:
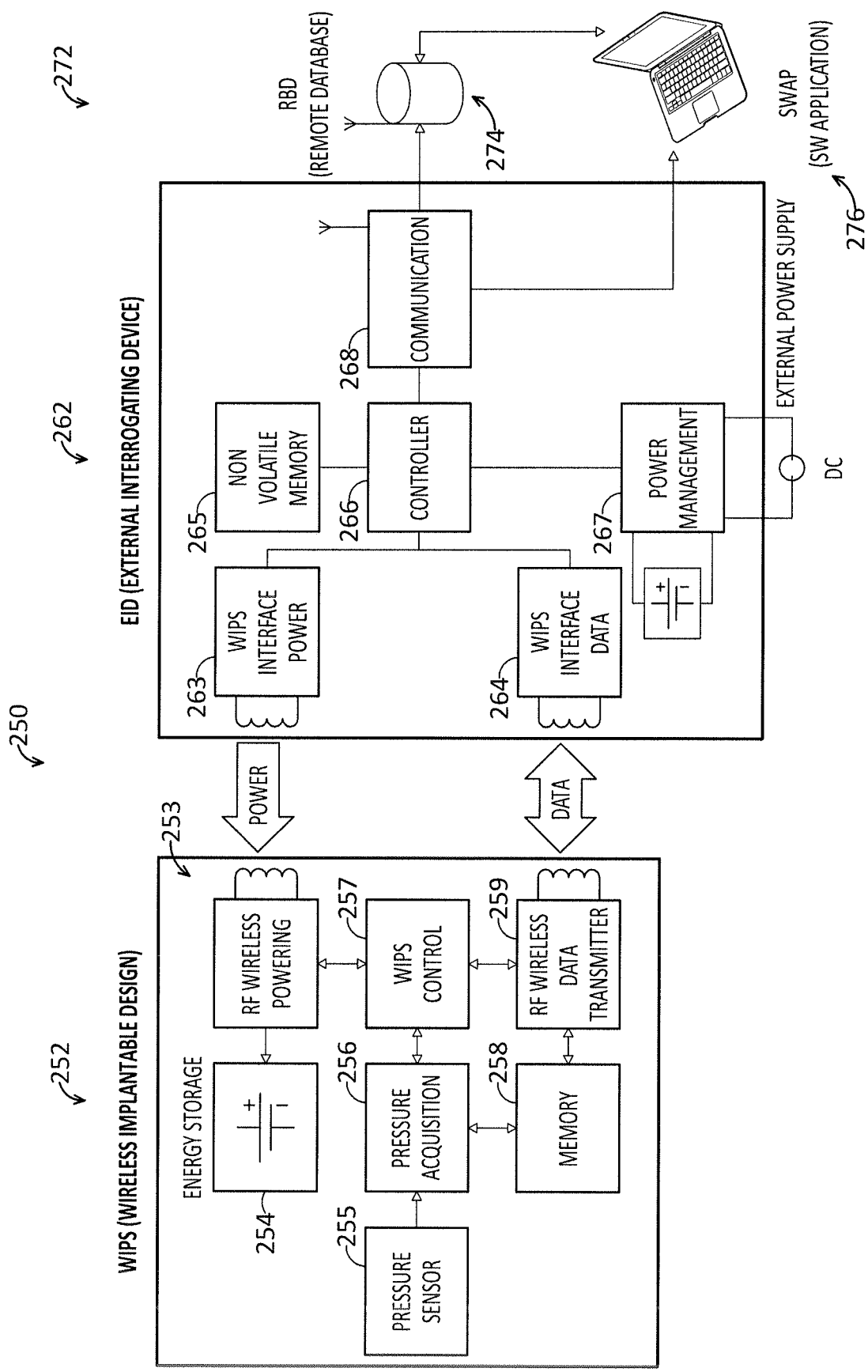
FIG. 17 illustrates a merely exemplary schematic of operation of an exemplary autonomous intraocular pressure sensor system.

The one or more remote databases can be a repository of all patient data, supplied by care givers, and encrypted; scalable; compatible with HIPPA regulations; and accessible to third parties FIG. 17 illustrates a merely exemplary schematic of operation of an exemplary autonomous intraocular pressure sensor system. System 250 includes implant 252, one or more EID 262, remote database 274, and SWAP 276. Not all aspects of the system need to be included in the system. Implant 252 (which can be any implant herein), includes wireless powering device 253 (e.g., RF powering), energy storage 254 (e.g., rechargeable battery), processor 257 (e.g., ASIC), pressure sensor 255, pressure acquisition software 256, memory 258, and data transmitter 259 (e.g., RF data transmitter). EID 262 can provide power to implant 252, and can have directional data transfer with implant 252. EID 262 includes power interface 263, data interface 264, controller 266, non-volatile memory 265, power management 267, and communication module 268 (e.g., wireless comm module).

Figure 21:
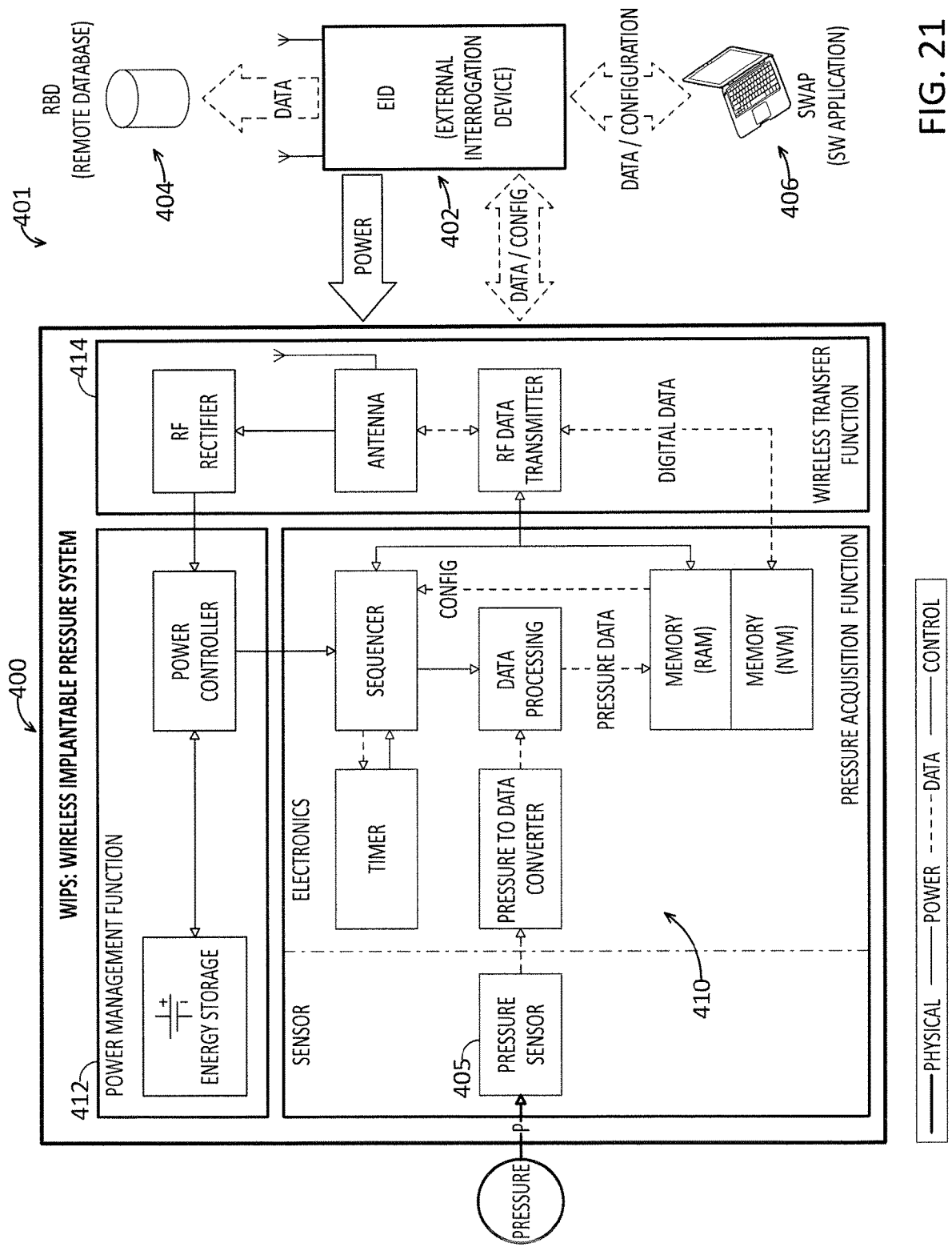
FIG. 21 illustrates a further exemplary schematic of operation of an exemplary autonomous intraocular pressure sensor system.

FIG. 21 illustrates a further exemplary schematic of operation of an autonomous intraocular pressure sensor system 401, including implant 400, EID 402, database 404 and SWAP 406. As shown, pressure sensor 405 senses pressure and sensed pressure or data is communicated to electronics 410. Power management 412 is in communication with wireless transfer function 414 and electronics 410. EID 402 can have any functionality described herein.

The disclosure herein also includes methods of delivering, or inserting, any of the implants herein. The disclosure herein also describes one or more surgical tools adapted for implanting the implant in or on the eye of a patient, and optionally a similar set of tools for implantation in animals for the purpose of validation studies. It is important that the implant, during delivery and after being implanted, not touch the corneal epithelium since the epithelial cells will be destroyed if they are touched.

The implantation of any of the implants herein in an eye will generally require one or more dedicated surgical tools and procedures. These implantation procedures will generally lead to minimal to no degradation of the patient's vision (e.g., by inducing astigmatism). In view of this, implantation through a needle (e.g., large gauge) is preferred over an incision. In some embodiments the entire implant is delivered through a needle. In some embodiments the needle is 13G needle, and in some embodiments it can be a 19-21G needle. An exemplary benefit of delivering through a needle is that no suturing is needed because no incision needs to be made.

Alternatively, the implantation of any implant herein can be combined with another surgical intervention, such as IOL implantation or in conjunction with other glaucoma drainage devices. In those embodiments, the implant and method of implant should be compatible with the incision already required for the implantation (e.g., IOL). In case of malfunction and/or risk to the patient, the implant is preferably also explantable with a similar, minimal invasive surgery, using dedicated tools. All tools and procedures are preferably compatible with both the right and left eye.

The implant is ideally positioned such as to not cause any visual obstruction, no degradation of any function of the eye, and generally not alter or aggravate the IOP of the patient (although some minor change in IOF may be caused). Additionally, in some embodiments, the implantation procedure does not deteriorate the vision of the patient by more than 0.25 diopters. An injection of the device (punch rather than incision) is preferred.

Figure 18:
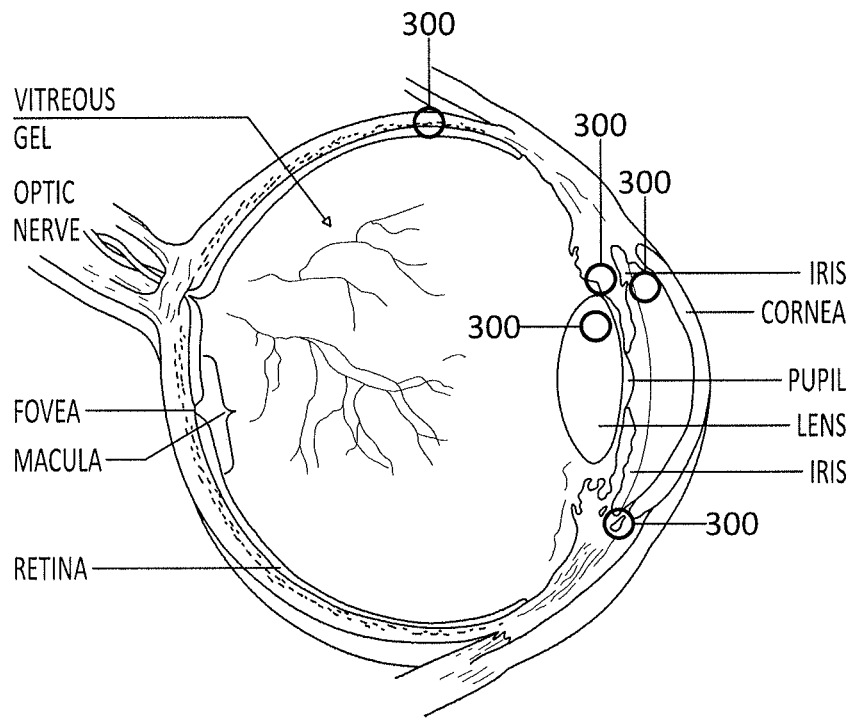
FIG. 18 illustrates exemplary implant locations, including but not limited to the anterior and posterior chamber, below the conjunctiva, and in Schlemm's canal.
Figure 19A:
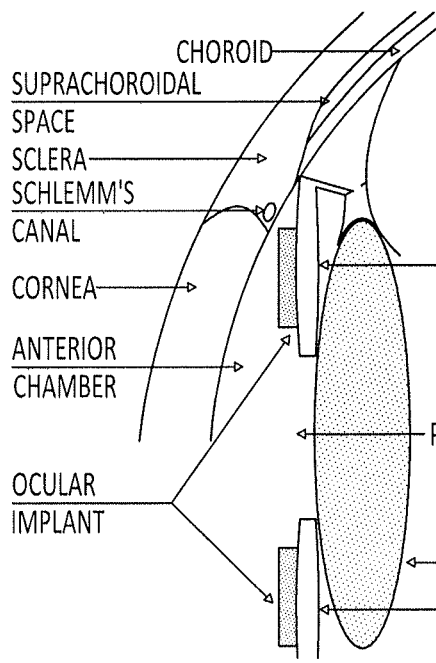
FIGS. 19A and 19B (side and front views, respectively) illustrates the anatomy of a portion of the eye, illustrating exemplary locations for the one or more implants.
Figure 19B:
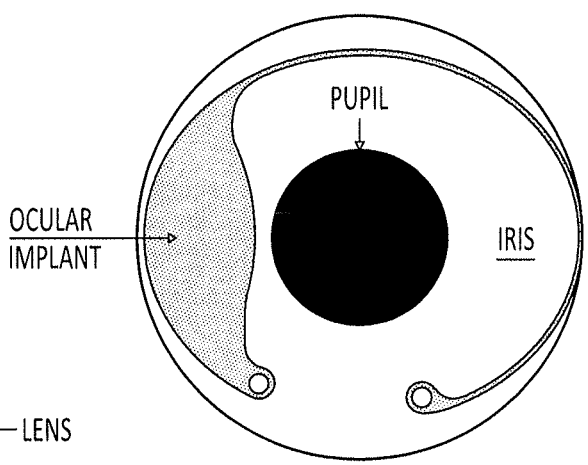

FIG. 18 illustrates exemplary implant locations 300, including but not limited to the anterior and posterior chamber, below the conjunctiva, and in Schlemm's canal. FIGS. 19A and 19B (side and front views, respectively) illustrates the anatomy of a portion of the eye, illustrating possible locations for the one or more implants. In some embodiments the implant includes two portions spaced from each other, and the implant is sized and configured such that the pressure sensor can be positioned in the anterior chamber while the implant housing is positioned in the suprachoroidal space. In some embodiments the implant is stabilized in placed due to, at least partially, the configuration of one or more components of the implant, and the interface with a portion of the eye. In some embodiments, fibrotic response can assist in keeping the implant, or a portion of the implant, in place.

Exemplary implantation procedures will now be disclosed. These exemplary procedures include an implantation of the sensor part of the implant in the anterior chamber angle, while the rest of the implant is positioned in the scleral/suprachoroidal space. These exemplary procedures include a punch incision and can be performed either at a slit lamp or in an operating room. The individual in which the implant is implanted is referred to generally herein as "patient," but can include any person or animal, whether suffering from a medical condition or not. An eye may have more than one implantable device implanted therein. For example, it may be beneficial to have multiple devices in different locations to sense pressure at different locations within the eye, particularly if pressure varies from location to location within the eye.

A first exemplary procedure includes implantation through the conjunctiva. An eye is prepped with Betadine 5% sterile Ophthalmic solution. Topical anesthesia is then instilled to the surface of the eye. Lidocaine 1% preservative free solution is then injected under the conjunctiva in the area of insertion of the implant. The patient will then look opposite to the site of insertion (e.g., a patient looks up for insertion of the implant in inferior quadrants). The insertion device (e.g., needle) holding the sensor is entered through the conjunctiva approximately 3.5 mm from the limbus, into the sclera 2.5 mm from the limbus, and then directed to the anterior chamber angle. Once the sensor in observed in the anterior chamber, the needle is withdrawn and the tail of the implant will remain within the sclera with the sensor portion in the anterior chamber angle. The entrance of the needle will be watertight and there will be not be a need for suturing.

A second exemplary procedure includes implantation through cornea/paracentesis. An eye is prepped with Betadine 5% sterile Ophthalmic solution. Topical anesthesia is then instilled to the surface of the eye. Lidocaine 1% preservative free solution is injected in the anterior chamber. A paracentesis is then made opposite to the area of insertion of the implant. The insertion device then enters through the paracentesis and is advanced to the opposite angles, and the tail of the implant is inserted in the suprachoroidal space with the sensor portion of the implant remaining in the anterior chamber angle. The inserter is removed from the eye and the paracentesis is watertight and there is no need for suture placement.

When used in humans, the implantation of a wireless implant with sensor may be used to improve a patient's glaucoma treatment, either for early diagnostics or at the medication stage. The implants may also be used to gather data, whether in animals or humans.

Taking into account that patient compliance is one of the major challenge in IOP treatment, and in view of the average age of glaucoma patients, the periodic (e.g., regular) measurements of the IOP are preferably done with minimal patient actions (autonomously). The preferred implementation of this is through an active implant, which carries out measurements at optionally fixed time intervals utilizing an internal power source/power storage and internal memory/data storage, and is read out on a less regular basis by one or more EIDs, or alternatively with an EID which is capable of performing remote measurements at such a range that the patient is free in their movements and daily activities. In some embodiments the data transmission to physician EID can occur autonomously. For example, sensed data can be autonomously transmitted from the implant to a bedside EID at night, and then autonomously transmitted.

After implantation, the implant sensor senses pressure. Pressure can be sensed continuously (sensed during the entire time the implant is positioned in the patient, without interruption), or non-continuously. The implant can optionally have a continuous sensing "mode," in which the implant is adapted to sense continuously, but the implant can also be taken out of the continuous mode, when switched to a different mode (e.g., no sensing, or a non-continuous sensing mode). When sensed non-continuously, it can be sensed periodically, either at regular intervals or non-regular intervals (e.g., sensed in response to detected events that do not happen with any known regularity). Exemplary regular intervals include one or more times a minute (e.g., 1, 2, 5, 10, 20, or 30 times a minute), one or more times a days (e.g., once, twice, five, twenty-four, 48 or 96 times a day). When sensed non-continuously, there may be epochs of time during which there is continuous sensing for a limited period of time, such as 1 minute of sensing, and then 59 minutes without sensing. An example of substantially continuous sensing is, for example, 30 times a minute. In some embodiments the pressure is sensed 1 time/day, or less (e.g., 1 time every two days). In some embodiments the frequency of sensing is between continuously and 2 times/day.

In some embodiments the implant is adapted to sense pressure at a particular frequency, but stores in memory only a subset of the sensed pressures. Sensed data can be stored in, for example, a first in first out manner.

The required IOP measurement pressure range can be, in some embodiments, 1 mmHg around ambient pressure and up to an overpressure of approximately 50 mmHg above ambient pressure.

The recorded data can be stored in a memory and transmitted periodically to an ophthalmologist (e.g., EID) for treatment evaluation. It may be beneficial for the patient not to have direct access to the IOP data. In some embodiments, in which the patient has an EID, the patient's EID is adapted to do one or more of the following: retrieve stored IOP data from the IOP implant; retrieve operational status of the implant and any error messages; and transfer power to the IOP implant to charge the power storage component.

In embodiments in which an IED provides power and data transfer to the implant, they are both preferably achieved wirelessly, typically over an RF link. The EID can receive this data and status of the implant, and communicate it to the ophthalmologist (or other second EID) for treatment evaluation support. In addition, the data collected by any or all EIDs can be compiled in databases, optionally in an anonymized format, in order to use the collective patient data to support applications in predictive medicine and e-health.

In embodiments in which medical personnel have access to an EID, that EID can be adapted to perform the same tasks as the patient EID, but it may additionally be adapted to perform any of the following: program some basic operational functions of the implant (e.g., measurement interval), and allow calibration of the implant's IOP values against e.g., a traditional tonometer.

In some embodiments an external interrogation unit has a resonant circuit for wireless charging of the implant; ASIC for power and data management; can be mounted in furniture, bed, eyeglasses for close access to the implant coil; adapted to reprogram the firmware, algorithm in the implant; can have multiple units for patient convenience; and can be portable.

Sensor readings from one or more implants may need to be calibrated based on, for example, their position in the eye. In some embodiments the position of the one or more wireless IOP sensors is such that the pressure reading at the sensor is directly linked to, or can be calibrated back to, the fluid pressure in the anterior chamber. Currently, intraocular pressure is measured by a device applying a force to the anterior surface of the cornea. It may be that sensor readings sensed within the eye, or even at different locations within the eye, result in pressure sensor readings that are different than are currently measured at the anterior surface of the cornea. Sensor readings obtained with implants herein may thus need to be calibrated with existing pressure readings taken at the anterior surface of the cornea. Different sensor locations may also need to be calibrated individually, particularly if sensor readings are different at different locations within the eye. Additionally, pressure readings may be more accurate or provide more reliable information at particular locations within the eye.

Patient to patient variability, which can be variability across the board or at particular locations, can require calibration and/or recalibration for each patient.

In some embodiments more than one sensor may be implanted in an eye, and the different sensors may obtain unique sensor readings. The system can be adapted to use the different sensor data to, for example, provide a pressure difference between two sensors, and improved patient therapy or diagnostics.

In some embodiments, in order to use the collected pressure data (patient-specific or anonym ized), a remote database (e.g., cloud database) of the recorded IOP values exists. The database can interact with one or more EIDs and/or clinicians, and can be used to process the IOP data.

While the implant generally only communicates when interrogated by an EID (due to power constraints), in some modified embodiments the implant may be adapted with sensed data event detection, generally requiring a processing component. For example, when sensing pressure, the implant can be adapted to detect a threshold pressure or other event. The event detection can trigger a variety of actions, such as, for example, automatic drug delivery, storing future sensed data after the detected event, and automatic transmission of data to one or more EIDs.

In some embodiments the implant and one or more EIDs can be adapted so that the one or more EIDs can reprogram one or more functions of the implant. For example, an implant's sensing frequency, event detection, sensed threshold value, etc., can be reprogrammed by the one or more EIDs. Reprogramming can occur in response to a change in the database lookup tables, for example. Reprogramming can also occur in response to data sensed from the particular patient.

Any of the implants herein can have an internal power source that can be recharged using an EID. In some embodiments charging is done via an inductive or electromagnetic coupling with emitted powers from the EID in the 10-30 mW range, such as 25 mW, or in the range of 1 W to 5 W, such as 3 W. In some embodiments the EID can transmit power and data to the implant.

In some embodiments the length of the antenna in the implant is 30 mm or less, such as 25 mm or less, such as 15 mm or less, such as 10 mm or less, and a height of 3 mm or less, such as 2.0 mm or less, such as 1.5 mm or less.

This exemplary power transfer data shows feasibility for these antenna designs, with the exemplary coiled antennas more efficient than the straight antenna. Initial prototypes have used the MIL-STD 883 for hermeticity requirements. The norm specifies 5000 ppm of $H_2O$ vapour as upper limit. Rationale: 5000 ppm is condensation point of water vapour at 0 deg C. With less than 5000 ppm of $H_2O$, water will never condensate: above 0 deg C it is vapour, below 0 deg C the condensed water will freeze. No liquid water can be present below 5000 ppm at any temperature. Note: At eye temperature, the dew point is much higher than 5000 ppm, namely 25000 ppm.

The following describes some optional features of any of the implant housings (e.g., around a battery and ASIC) herein: Any of the implants herein can achieve <5000 ppm $H_2O$ over a 10 year lifetime. There may be a trade-off between housing thickness and permeability: thicker housing walls provide lower permeability but cause a larger implant volume. A larger inner volume gives more allowed $H_2O$ before reaching 5000 ppm but for larger implant volume. It may be preferable for the housing material for electronics and battery to be glass, ceramic or metal (Ti) or any metal/glass/ceramic combination. Additional conformal barriers like Parylene C are also considered. Any of the implants herein can include a $H_2O$ getter. $H_2O$ getter can be a solid/polymer that binds $H_2O$ molecules entering implant, lowering internal $H_2O$ pressure (until full). The $H_2O$ getter can extend lifetime below 5000 ppm at a given permeability.

The disclosure herein includes methods of use in animals (e.g., rabbits, mice, rat, dog) aimed at initial IOP data collection and serving for validation studies for humans or veterinary applications. The disclosure herein also includes human uses, which can be aimed at collecting regular patient IOP values to be used for any of diagnostics support, drug selection support, and evaluation of patient compliance to glaucoma treatment. The rabbit eye is a standard biomedical model for validating human intraocular implants as it has similar dimensions (see FIGS. 20A-20B), but shows accelerated fibrotic and inflammatory behavior with respect to human eyes. Any of the WIPS herein can thus be implanted in rabbit (or other animal) eyes. The implantation of implantable device in animals can provide any of the following: data can be gathered for glaucoma pharmaceutical development programs; data collected by a device in a rabbit's eye can be used as clinical evidence for a future human product; and valuable usability inputs can be generated.

Figure 20A:
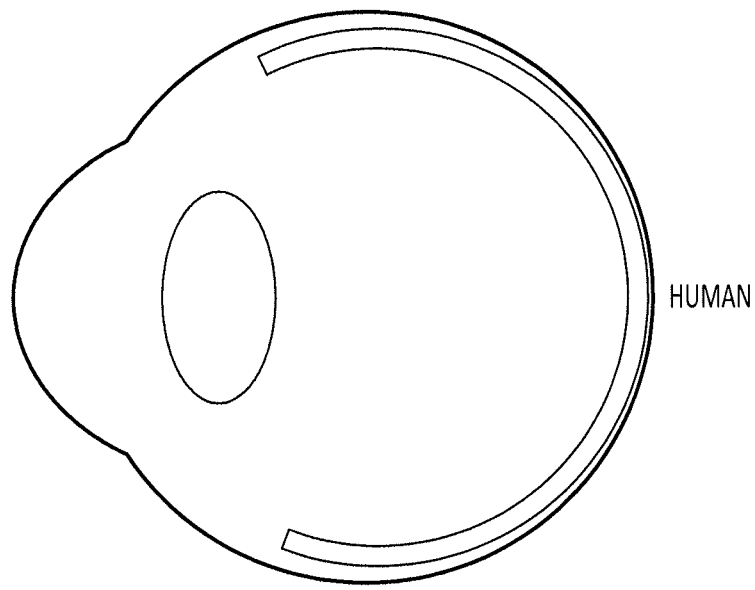
FIGS. 20A and 20B show human (a), and rabbit eye (b) to scale.
Figure 20B:
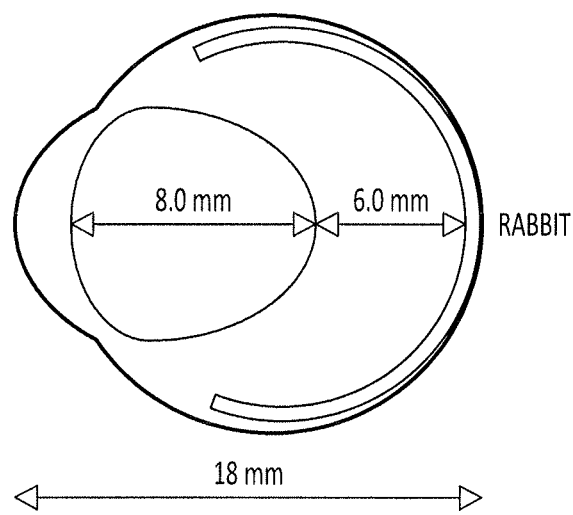

FIGS. 20A and 20B show human (a), and rabbit eye (c) to scale, including schematic representation of the lens (yellow), retina (red) and vitreous and aqueous bodies (blue).

An IOP device that is implanted in a rabbit should therefore, in some uses, be the same or nearly the same as a current or future human device. Some difference between rabbit implants and human implants may include one or more of: the implant location in a rabbit eye may be different than in the human eye in view of the dimensional differences of anterior and posterior chamber of a human vs. rabbit eye (the location should be, however, medically representative (IOP, fibrosis, inflammation)); the implantation time may be shorter with the rabbit compared to the human application; the surgical tools may differ in size to match the dimensions of the rabbit's eye, but not in function compared to the tools for human implantation; and the regulatory requirements that apply for rabbit implantation may differ from those for human implantation. All other aspects can be the same as those of human implants described in the following section.

The system and implants herein can also be used for research purposes to investigate changes in intraocular pressure due to certain activities, such as exercise, or sleep, or drug therapy.

Additional Examples. The following are additional examples of the disclosure herein.

An optionally autonomous, wirelessly connected, intraocular pressure sensing implant, wherein said implant is less than 3.5 mm in its longest dimension.

The implant of any of the additional examples herein wherein said implant has an internal rechargeable power source that can provide operating power for at least one half day (12 h) of operation.

The implant of any of the additional examples herein wherein said power source is a rechargeable battery.

The implant of any of the additional examples herein wherein said implant has power and data management integrated circuits that consume less than 50% of its stored power in resistive losses.

The implant of any of the additional examples herein wherein said implant utilizes at least one application specific integrated circuit for power and data management.

The implant of any of the additional examples herein wherein said implant comprises a sensor that senses intraocular pressure and collects pressure data more than once every 12 hours and no more than once every minute.

The sensor of any of the additional examples herein wherein said sensor operates at a frequency of 30 Hz or more.

The implant of any of the additional examples herein wherein said ASIC is controlled by firmware that is reprogrammable by an external unit via wireless communication of data subsequent to implantation of any of the implants herein.

The implant of any of the additional examples herein wherein said ASIC downloads data to said external unit that is programmed to receive said data.

The implant of any of the additional examples herein wherein said ASIC actuates commencement of wireless recharging from said external unit upon receipt of a trigger signal.

The implant of any of the additional examples herein wherein a trigger signal may be transmitted from an external unit.

The implant of any of the additional examples herein wherein said trigger signal may be generated inside said ASIC when the output voltage of said rechargeable battery of claim 3 drops below a threshold voltage that is above the voltage at which the battery shuts down.

The implant of any of the additional examples herein wherein said implant is rendered biocompatible by being hermetically sealed.

The implant of any of the additional examples herein wherein said sensor is periodically actuated by an ASIC.

The implant of any of the additional examples herein wherein a trigger can be externally or internally generated.

The implant of any of the additional examples herein wherein a trigger signal when internally generated, is reprogrammable.

The implant of any of the additional examples herein wherein data is processed and filtered in firmware in an ASIC.

The implant of any of the additional examples herein wherein data is further processed, analyzed and encrypted in a data processing module in an external unit.

The implant of any of the additional examples herein wherein data is downloaded to a smart phone or a tablet or a dedicated electronic device (e.g., the EID).

The implant of any of the additional examples herein wherein data is transmitted from an EID, a smart phone or a tablet to the computer of the caregiver.

The implant of any of the additional examples herein wherein data is transmitted by the caregiver to a remote data base.

An implant sized to be stabilized within an eye, the implant comprising an intraocular pressure sensor.

An implantable intraocular pressure sensor, comprising a pressure sensor and electronics coupled to the pressure sensor.

Any of the claimed implants, adapted to be positioned in any of the anatomical shows or described herein.

A method of positioning an intraocular pressure implant, comprising a sensor, in an eye.

A method of sensing intraocular pressure continuously, substantially continuously, or periodically, with an implantable intraocular sensor sized and configured to be stabilized within an eye.

Any of the claimed methods, further comprising transmitting information, either pressure data (e.g., raw or processed) or information indicative of pressure data wirelessly to an external device.

Any of the methods of calibrating an implantable pressure sensor herein.

A method of sensing pressure in an eye with an implantable device, wherein the implantable device is adapted to process the sensed pressure.

The implant of any of the additional examples herein wherein the implant comprises a memory module that further comprises non-erasable and/or reprogrammable memory elements.

The implant of any of the additional examples herein wherein the implant comprises a controller that controls its pressure sensing, data collection, processing, storage and transmission, and recharging operations.

The implant of any of the additional examples herein wherein a wireless connection between said implant and an external unit is operated at below 6 GHz, e.g., at 868 MHz, 900 MHz or 2.4 GHz.

The implant of any of the additional examples herein wherein the wireless connection between implant and external unit comprises electro-magnetic or inductive coupling between a transmitting and a receiving antenna.

The implant of any of the additional examples herein wherein the wireless connection between implant and external unit utilizes one or more antennas which can be e.g., straight, coiled, or flat.

The implant of any of the additional examples herein wherein the wireless connection between implant and external unit coupling has a system Q factor not less than 10 and not exceeding 100.

The implant of any of the additional examples herein wherein a transmitter coil transmits wireless power not exceeding 25 milliwatts.

The implant of any of the additional examples herein wherein recharging of the implant occurs at any distance between 2 cm and 2 meters.

The implant of any of the additional examples herein wherein preferred modes of charging the implant are either at 2-5 cm over 1 hour or 0.5-2.0 meters over 8 hours.

The implant of any of the additional examples herein wherein data is transmitted by the EID, the patient's smartphone or tablet to a remote data base.

The invention claimed is:

1. A hermetically sealed implantable pressure sensor assembly adapted to wirelessly communicate with an external device, comprising:
    a casing comprising a titanium layer; and
    a hermetically sealed housing, the hermetically sealed housing including therein:
        an antenna in electrical communication with a rechargeable power source,
        the rechargeable power source in electrical communication with an application-specific integrated circuit (ASIC), and
        the ASIC in electrical communication with a pressure sensor;
    wherein said titanium layer is coated with an electrically insulating ceramic layer wherein said ceramic layer has lattice constants that match those of titanium.

2. The assembly of claim 1, wherein the antenna is part of a first circuit adapted to supply power to the rechargeable power source, and the antenna is also part of a second circuit adapted to transmit data to the external device.

3. The assembly of claim 1, further comprising a flexible circuit, the flexible circuit in electrical communication with the pressure sensor and the ASIC.

4. The assembly of claim 3, wherein the flexible circuit is in electrical communication with the antenna and the power source.

5. A hermetically sealed implantable pressure sensor assembly adapted to wirelessly communicate with an external device, comprising:
    a casing comprising a titanium layer; and
    a hermetically sealed housing, the hermetically sealed housing including therein:
        an antenna in electrical communication with a rechargeable power source,
        the rechargeable power source in electrical communication with an application-specific integrated circuit (ASIC), and
        the ASIC in electrical communication with a pressure sensor;
    wherein said titanium layer is coated with a hydrogel layer, wherein said hydrogel layer has a gradient in cross-link density.

6. The assembly of claim 5 wherein said hydrogel layer has a gradient in number density of hydroxyl groups, said gradient being in an opposite direction of a gradient in cross-link density.

7. The assembly of claim 5 wherein said hydrogel layer is impregnated with an anticlotting agent.

8. The assembly of claim 5 wherein said hydrogel layer is impregnated with an anti-inflammatory agent.

9. The assembly of claim 5, wherein an outer surface of the hydrogel layer is textured to stimulate a controlled fibrotic response.

10. The assembly of claim 5, wherein the hydrogel layer is infused with at least one of an anti-inflammatory agent and an anticlotting agent.

11. The assembly of claim 5, wherein said hydrogel layer is chemically bonded to medicaments that are slowly and sustainably released into an eye over a period of not less than 10 days.

12. The assembly of claim 9, wherein the textured outer surface of the hydrogel layer includes a plurality of depressions, each of which have a height between 5 microns and 15 microns.

13. The assembly of claim 1 wherein said pressure sensor comprises a hermetically sealed module comprising an inert fluid situated inside said module.

14. A hermetically sealed implantable pressure sensor assembly adapted to wirelessly communicate with an external device, comprising:
    a hermetically sealed housing, the hermetically sealed housing including therein:
        an antenna in electrical communication with a rechargeable power source,
        the rechargeable power source in electrical communication with an application-specific integrated circuit (ASIC), and
the ASIC in electrical communication with a pressure sensor,
    wherein said pressure sensor comprises a hermetically sealed module comprising an inert fluid situated inside said module, and
    wherein said hermetic seal encasing said pressure sensor comprises a Titanium foil of thickness in a range of 5-25 microns, said foil being undulated to enhance its surface area and resistance to mechanical stress.

15. The assembly of claim 14, wherein said pressure sensor comprises a piezoelectric sensing element wherein said inert fluid transmits hydrostatic pressure to said sensing element through said Titanium foil.

16. The assembly of claim 14, wherein said pressure sensor comprises a capacitive sensing element wherein said inert fluid transmits hydrostatic pressure to said sensing element through said Titanium foil.

17. The assembly of claim 14, wherein said sensor is of dimensions of length 0.2 mm to 1.5 mm in length, 0.2 mm to 0.7 mm in width and 0.1 mm to 0.7 mm in thickness.

18. The assembly of claim 1 wherein said antenna comprises a space filling design, wherein the antenna is connected to an electrical circuit that can be adjusted for its electrical impedance as a function of its resistive load.

19. The assembly of claim 18, wherein said antenna is disposed on a ceramic substrate situated inside said casing, wherein said antenna has a thickness in a range of 100-500 microns.

20. The assembly of claim 18, wherein said circuit comprising said antenna has a Q factor in a range of 10-50 under use conditions.

21. The assembly of claim 18, wherein said antenna is comprised of vacuum deposited metal filaments on a ceramic substrate.

22. The assembly of claim 18, wherein said antenna provides both data transfer and energy transfer functions.

23. The assembly of claim 18, wherein said antenna comprises a conductive length of no less than 15 mm and no more than 100 mm.

24. The assembly of claim 18, wherein said antenna transmits electromagnetic energy at a frequency that is not harmful to a human body.

25. The assembly of claim 1, wherein said ASIC comprises a microelectronic circuit comprising a microcontroller, a flash memory, a non-volatile memory and a logic circuit.

26. The assembly of claim 25, wherein said logic circuit comprises power management and data management modules.

27. The assembly of claim 25, wherein said ASIC comprises a microelectronic circuit wherein said microelectronic circuit comprises conductive connectors of width in a range of 36-360 nanometers.

28. The assembly of claim 1, wherein the assembly has a length not greater than 4.8 mm, a height not greater than 1.5 mm, and a width not greater than 1.5 mm.

29. The assembly of claim 1, wherein the pressure sensor is disposed inside of a fluid filled chamber.

30. The assembly of claim 29, wherein the fluid filled chamber includes a flexible membrane adapted to transmit pressure from an external environment to a fluid within the fluid filled chamber.

31. The assembly of claim 30, wherein the flexible membrane is 5-20 microns thick.

32. The assembly of claim 30, wherein the flexible membrane is selected from the group consisting of titanium and parylene.

33. The assembly of claim 1, wherein the pressure sensor is adapted to sense intraocular pressure more than once every 12 hours and no more than once every 10 milliseconds, and wherein the ASIC is adapted to facilitate storage of pressure data more than once every 12 hours and no more than once every 10 milliseconds.

34. The assembly of claim 1, further comprising the external device in wireless communication with the assembly, wherein the external device has a communication component that is adapted to transmit a wireless signal to the assembly indicating its readiness to receive data from the assembly and provide wireless power to the assembly, and wherein the ASIC is adapted to acknowledge the transmitted wireless signal with one of at least two different signals, indicating its readiness to transmit or receive data and its readiness to receive wireless power.

35. The assembly of claim 1, wherein the ASIC has a communication component that is adapted to transmit pressure data from the implantable assembly to the external device, wherein the external device has a communication component that is adapted to receive the transmitted pressure data, wherein the ASIC is adapted to transmit the pressure data upon receiving a trigger signal from the external device and after acknowledging receipt of the trigger signal.

36. The assembly of claim 1, wherein the ASIC has a communication component that is adapted to transmit pressure data from the implantable assembly to the external device, wherein the external device has a communication component that is adapted to receive the transmitted pressure data, wherein the ASIC is adapted to transmit the pressure data upon receipt of an acknowledgment signal from the external device of receipt of a trigger signal from the implantable assembly.

\* \* \* \* \*